(12) United States Patent
Prat et al.

(10) Patent No.: US 8,258,328 B2
(45) Date of Patent: Sep. 4, 2012

(54) METHOD AND INTERMEDIATES FOR PREPARING 19-NORSTEROID COMPOUNDS

(75) Inventors: Denis Prat, Pantin (FR); Christian Moratille, Bry sur Marne (FR); Francoise Benedetti, Rosny sous Bois (FR); Lahlou Nait-Bouda, Bondy (FR)

(73) Assignee: Aventis Pharma S.A., Antony (FR)

(*) Notice: Subject to any disclaimer, the term of this patent is extended or adjusted under 35 U.S.C. 154(b) by 0 days.

(21) Appl. No.: 12/915,966

(22) Filed: Oct. 29, 2010

(65) Prior Publication Data

US 2011/0046402 A1 Feb. 24, 2011

Related U.S. Application Data

(63) Continuation of application No. 10/834,749, filed on Apr. 29, 2004, now abandoned.

(30) Foreign Application Priority Data

Apr. 29, 2003 (FR) ...................................... 03 05221

(51) Int. Cl.
  *C07J 1/00* (2006.01)
  *C07J 43/00* (2006.01)
(52) U.S. Cl. ........................................ 552/626; 540/113
(58) Field of Classification Search .................. 552/626; 540/113
  See application file for complete search history.

(56) References Cited

U.S. PATENT DOCUMENTS

| | | | |
|---|---|---|---|
| 3,275,623 A | 9/1966 | Knox | |
| 5,478,957 A | 12/1995 | Godard et al. | |
| 5,556,965 A | 9/1996 | Godard et al. | |
| 6,207,657 B1 | 3/2001 | Bouali et al. | |
| 6,239,121 B1 | 5/2001 | Bouali et al. | |
| 6,423,700 B1 | 7/2002 | Bouali et al. | |
| 6,479,476 B1 | 11/2002 | Nique | |
| 6,482,813 B1 | 11/2002 | Bouali et al. | |
| 7,381,718 B2 | 6/2008 | Benedetti et al. | |
| 7,449,572 B2 | 11/2008 | Nique et al. | |

FOREIGN PATENT DOCUMENTS

| | | | |
|---|---|---|---|
| FR | 2640977 | | 6/1990 |
| GB | 1228211 | | 4/1971 |
| WO | WO 02/100880 | * | 12/2002 |

OTHER PUBLICATIONS

Larkin et al., The Synthesis of 17alpha-Methyl-11beta-Arylestradiol: Large Scale Application of the Cerium (III)-Mediated Alkylation of a Ketone, Organic Process Research & Development (2002, pp. 20-27, vol. 6, No. 1).

* cited by examiner

*Primary Examiner* — Barbara P Badio
(74) *Attorney, Agent, or Firm* — Harness, Dickey & Pierce, P.L.C.

(57) ABSTRACT

The subject of the invention is a method for preparing compounds of general formula (I):

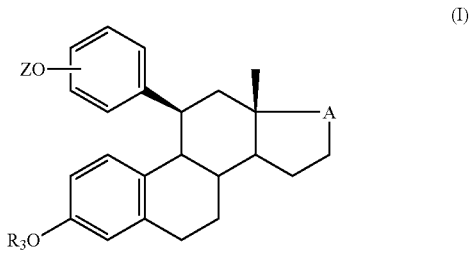

in which A, Z, $R_3$ are as defined in the description, and the intermediate compounds for carrying out this method.

31 Claims, No Drawings

METHOD AND INTERMEDIATES FOR PREPARING 19-NORSTEROID COMPOUNDS

This application is a continuation of U.S. patent application Ser. No. 10/834,749, filed Apr. 29, 2004 which is now abandoned and claims the benefit of priority of French Patent Application No. 03/05,221, filed Apr. 29, 2003. The entire disclosures of each of the above applications are incorporated herein by reference.

BACKGROUND OF THE INVENTION

1. Field of the Invention

The subject of the present invention is a method for preparing 19-norsteroid compounds, and the intermediate compounds prepared during the use of this method.

2. Description of the Art

Osteoporosis is a bone disease which affects 50 million people worldwide, more particularly women. Its development is linked to age and begins most often after the menopause. This disease is characterized by a reduction in bone density, causes deformations, vertebral compression and in time spontaneous fractures. Osteoporosis therefore represents a serious challenge for public health. The main treatment consists in taking estrogens regularly, which reduces bone loss but which, nevertheless, may be accompanied by certain side effects (bleeding, hot flushes, risk of breast cancer, and the like). A novel series of molecules called SERM (Selective Estrogen Receptor Modulator) allows the treatment of osteoporosis while avoiding some of the side effects (WO98/45316, WO99/67274, WO98/28324, WO99/25725, EP605193, WO02/100880).

The subject of the present application is the development of a novel method for preparing a key intermediate (compound of formula I) in the synthesis of certain estrogen derivatives having a dissociated activity.

All of the references described herein are incorporated herein by reference in their entirety.

SUMMARY OF THE INVENTION

The subject of the invention is a method for preparing compounds of general formula (I):

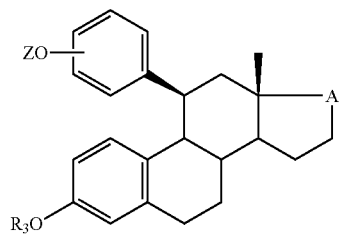
(I)

in which
Z represents a linear alkyl radical or a group $R_4$ of the formula:

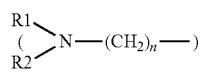
$R_4$ in which n is an integer from 2 to 8, and either $R_1$ and $R_2$, which are identical or different, represent a benzyl group or a linear, branched or cyclic alkyl, alkenyl or alkynyl radical containing from 1 to 8 carbon atoms, or $R_1$ and $R_2$ taken together with the nitrogen atom to which they are attached form a saturated or unsaturated, aromatic or nonaromatic 5- to 6-membered heterocycle optionally containing from 1 to 3 additional heteroatoms and optionally fused with another ring, A represents a keto functional group or a group CH—X, X representing a halogen atom, $R_3$ represents a hydrogen atom or a group protecting the hydroxyl functional group, comprising the following steps:

a) the mixture of the compounds of formulae (IIIa) and (IIIb):

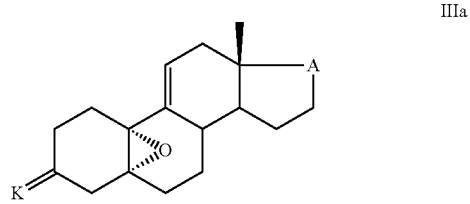
IIIa

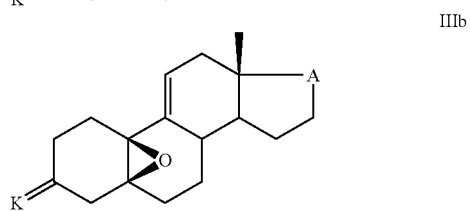
IIIb wherein =K representing a keto functional group protected in particular in ketal, thioketal or mixed ketal form, is subjected to an alkylation reaction with an organocuprate derivative derived from an organometallic compound of formula $R_5MgHal$ or $R_5Li$, Hal being a halogen atom and generated catalytically or stoichiometrically, in which $R_5$ represents the group:

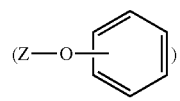

Z being as defined above, the bonding taking place on the phenyl, and then to the action of a deprotecting agent so as to obtain the compounds of formulae (Va), (Vb) and (Vc):

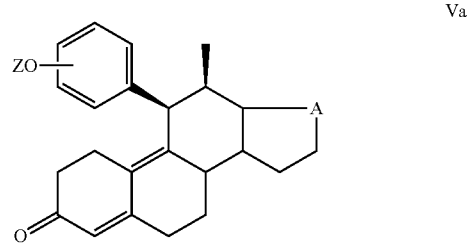
Va

-continued

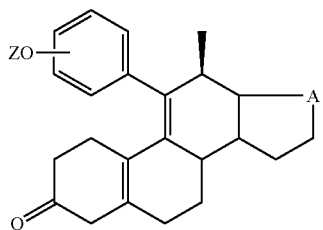

Vb

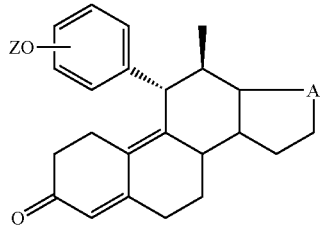

Vc b) the compounds of formulae (Va), (Vb) and (Vc) are treated with an aromatization agent so as to obtain the mixture of the compounds of formulae (VI) and (I):

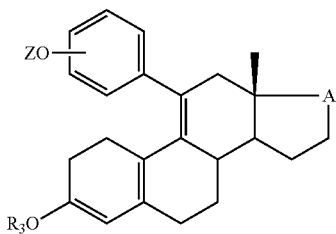

VI which continue to undergo aromatization so as to obtain the compound of formula (I), $R_3$ being as defined above.

The subject of the invention is also a method for preparing compounds of general formula (I):

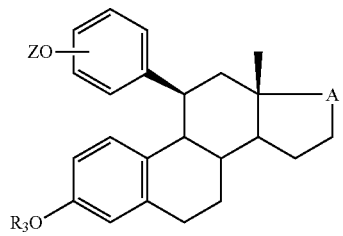

in which

Z represents a linear alkyl radical or a group $R_4$ of the formula:

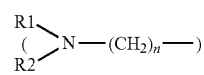

$R_4$ in which n is an integer from 2 to 8, and either $R_1$ and $R_2$, which are identical or different, represent a benzyl group or a linear, branched or cyclic alkyl, alkenyl or alkynyl radical containing from 1 to 8 carbon atoms, or $R_1$ and $R_2$ taken together with the nitrogen atom to which they are attached form a saturated or unsaturated, aromatic or nonaromatic 5- to 6-membered heterocycle optionally containing from 1 to 3 additional heteroatoms and optionally fused with another ring, A represents a keto functional group or a group CH—X, X representing a halogen atom, $R_3$ represents a hydrogen atom or a group protecting the hydroxyl functional group, comprising the following steps:

a) the compound of formula (IIIb):

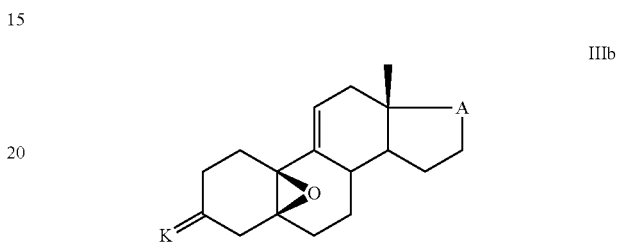

IIIb wherein =K representing a keto functional group protected in particular in ketal, thioketal or mixed ketal form, is subjected to an alkylation reaction with an organocuprate derivative derived from an organometallic compound of formula $R_5MgHal$ or $R_5Li$, Hal being a halogen atom and generated catalytically or stoichiometrically, in which $R_5$ represents the group:

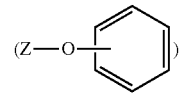

Z being as defined above, the bonding taking place on the phenyl, and then to the action of a deprotecting agent so as to obtain the compounds of formulae (Vb) and (Vc):

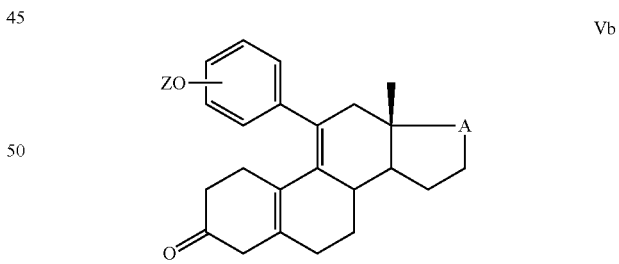

Vb

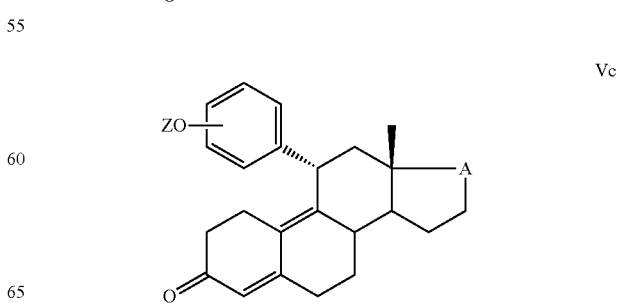

Vc b) the compounds of formulae (Vb) and (VC) are treated with an aromatization agent so as to obtain the mixture of the compounds of formulae (VI) and (I):

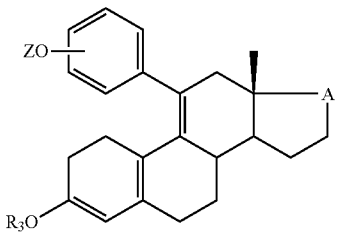

VI which continue to undergo aromatization so as to obtain the compound of formula (I), $R_3$ being as defined above.

The group (ZO—) may be at the ortho, meta or para position.

DETAILED DESCRIPTION OF THE INVENTION

As an example of a linear alkyl radical which Z may represent, there may be mentioned methyl, ethyl, propyl, butyl, pentyl, hexyl and octyl radicals. The linear alkyl radical which Z may represent is preferably methyl.

As an example of a linear or branched alkyl radical containing from 1 to 8 carbon atoms which $R_1$ and $R_2$ may represent, there may be mentioned methyl, ethyl, propyl, butyl, pentyl, hexyl and octyl radicals, and the branched isomers of these radicals, isopropyl, isobutyl, isopentyl, neopentyl, isohexyl, 3-methylpentyl, sec-butyl, tert-butyl and tert-pentyl. The preferred alkyl radicals are methyl and ethyl.

As an example of a cyclic alkyl radical which $R_1$ and $R_2$ may represent, there may be mentioned cyclopropyl, cyclobutyl, cyclopentyl, cyclohexyl, cycloheptyl and cyclooctyl radicals which may be substituted for example with an alkyl group containing from 1 to 4 carbon atoms.

As an example of an alkenyl radical which $R_1$ and $R_2$ may represent, there may be mentioned allyl, butenyl and 3-methyl-2-butenyl radical. As an example of alkynyl radicals, there may be mentioned the propargyl radical. Of course these alkenyl or alkynyl radicals contain at least 2 carbon atoms and are attached to the nitrogen atom via a group —$CH_2$—.

As an example of a heterocycle which $R_1$ and $R_2$ may form together with the nitrogen atom to which they are attached, there may be mentioned in particular mono- or bicyclic heterocycles optionally containing another heteroatom chosen from oxygen and nitrogen, such as the following unsaturated heterocycles: pyrrolyl, imidazolyl, indolyl, pyridyl, pyrazinyl, pyrimidinyl, pyridazinyl, thiazolyl, oxazolyl, furazolinyl, pyrazolinyl; or such as the following saturated heterocycles: morpholinyl, pyrrolidinyl, piperidinyl, oxazolidinyl, thiazolidinyl. It will be preferably the group:

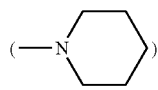

As an example of a halogen atom which Hal may represent, there may be mentioned chlorine, iodine or bromine.

As an example of a halogen atom which X may represent, there may be mentioned chlorine, bromine, iodine or fluorine. It is preferably fluorine.

As an example of a protecting group which $R_3$ may represent, there may be mentioned in particular a group ($C_1$-$C_6$)-alkyl, ($C_1$-$C_6$)-alkyl-CO— such as $CH_3CO$ or benzoyl, benzyl, phenyl-($C_1$-$C_6$)-alkyl such as benzyl, and all the protecting groups known to persons skilled in the art, for example those described in Greene, Wuts, Protective Groups in Organic Synthesis 3rd edition, Wiley & sons, 1999. Preferably $R_3$, by way of a protecting group, is an acyl group.

As an example of a group protecting the keto at the 3-position of the steroid which =K may represent, there may be mentioned cyclic ketals such as —O—$(CH_2)$, O—, —O—$(CH_2)_m$—S—, —S—$(CH_2)_m$—S—, —O—$CH_2C(C_{1-4}$-alkyl$)_2$-$CH_2$—O—, wherein m is an integer from 1 to 4.

acyclic ketals such as $(CH_3O)_2$, $(EtO)_2$, as well as all the groups protecting the keto group which are known to persons skilled in the art, for example those described in Greene, Wuts, Protective Groups in Organic Synthesis 3rd edition, Wiley & sons, 1999. Preferably, =K is a cyclic ketal, and in particular a 3,3-ethylenedioxy group.

As used herein the term "salinification" means subjecting the compound under consideration to a salt forming reaction so as to obtain a salt of said compound.

The subject of the invention is more particularly a method for preparing, as defined above, compounds of general formula (I) in which A is a keto functional group, comprising the following steps:

a) a compound of formula (II):

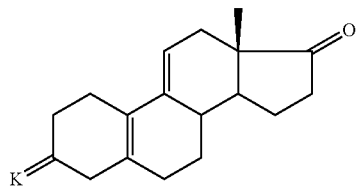

(II)

=K representing a keto functional group protected in particular in ketal, thioketal or mixed ketal form, is subjected to the action of an epoxidation reagent so as to obtain the mixture of the alpha and beta isomers of formulae (III'a) and (III'b):

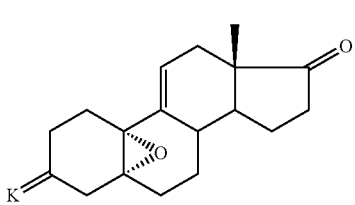

III'a

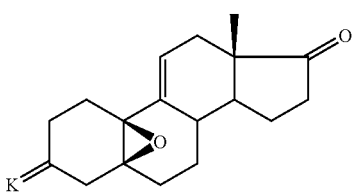

III'b b) the mixture of the compounds of formulae (III'a) and (III'b) is subjected to an alkylation reaction with an organocuprate derivative derived from an organometallic compound of formula R₅MgHal or R₅Li, Hal being a halogen atom and R₅ being as defined above, the bonding taking place on the phenyl, and then to the action of a deprotecting agent so as to obtain the compounds of formulae (V'a), (V'b) and (V'c):

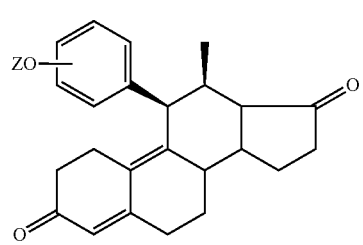

V'a

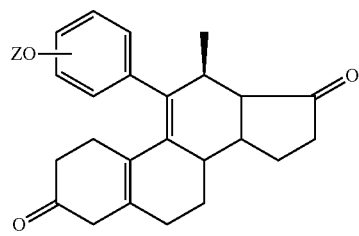

V'b

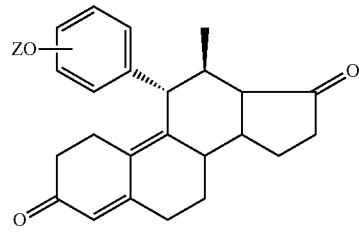

V'c c) the compounds of formulae (V'a), (V'b) and (V'c) are treated with a aromatization agent so as to obtain the mixture of the compounds of formulae (VI') and (I) in which A is a keto functional group:

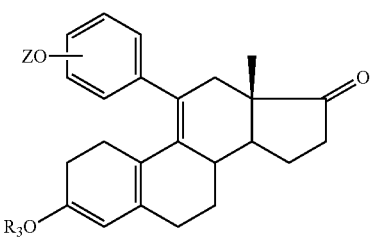

VI' which continue to undergo aromatization so as to obtain the compound of formula (I) in which A is a keto functional group, d) where appropriate, the product obtained in step c is deprotected so as to obtain a compound of formula (I) in which A is a keto functional group and R₃ represents a hydrogen atom, which is subjected, where appropriate, to a salinification reaction.

The subject of the invention is more particularly a method for preparing, as defined above, compounds of general formula (I) in which A is a keto functional group, comprising the following steps:

a) a compound of formula (II):

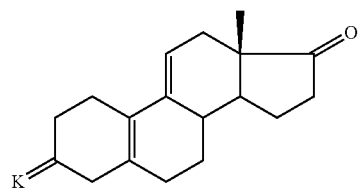

=K representing a keto functional group protected in particular in ketal, thioketal or mixed ketal form, is subjected to the action of an epoxidation reagent so as to obtain the beta isomer of formula (III'b):

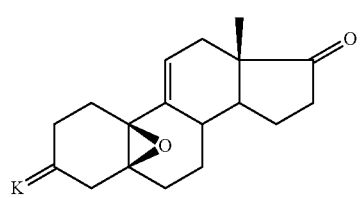

III'b b) the compound of formula (III'b) is subjected to an alkylation reaction with an organocuprate derivative derived from an organometallic compound of formula R₅MgHal or R₅Li, Hal being a halogen atom and R₅ being as defined above, the bonding taking place on the phenyl, and then to the action of a deprotecting agent so as to obtain the compounds of formulae (V'b) and (V'c):

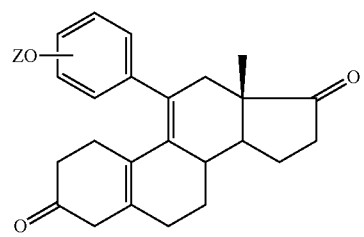

V'b

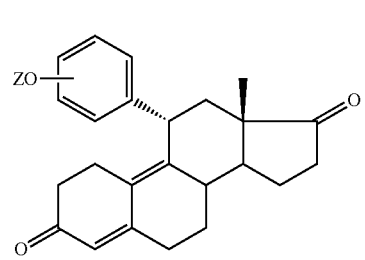

V'c c) the compounds of formulae (V'b) and (V'c) are treated with an aromatization agent so as to obtain the mixture of the compounds of formulae (VI') and (I) in which A is a keto functional group:

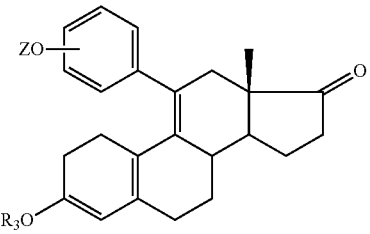

VI' which continue to undergo aromatization so as to obtain the compound of formula (I) in which A is a keto functional group, d) where appropriate, the product obtained in step c is deprotected so as to obtain a compound of formula (I) in which A is a keto functional group and $R_3$ represents a hydrogen atom, which is subjected, where appropriate, to a salinification reaction.

The epoxidation reaction is a standard reaction which is carried out according to methods known to persons skilled in the art. It may be carried out in particular in the presence of hexachloroacetone, dichloromethane and hydrogen peroxide.

The alkylation reaction with an organocuprate derivative derived from an organometallic compound of formula $R_5MgHal$ or $R_5Li$, Hal and $R_5$ being as defined above, is carried out according to standard methods known to persons skilled in the art.

The deprotection reaction which makes it possible to obtain the compounds of formulae (V'a), (V'c), or (V'b) is carried out according to standard methods known to persons skilled in the art. The deprotecting agent used is in particular an agent allowing acid hydrolysis, such as hydrochloric acid or perchloric acid.

The aromatization reaction is a standard reaction which is carried out in particular according to the methods described in EP 298,020. This aromatization may be carried out by catalysis with palladium, or preferably in the presence of acetyl bromide and acetic anhydride.

The deprotection of the acetyl group formed at the 3-position, where appropriate, is carried out in general in the presence of a strong base such as sodium hydroxide or potassium hydroxide, in an alcohol solvent, such as methanol or ethanol. It is preferably carried out in the presence of sodium hydroxide in methanol.

The salinification reaction is carried out by conventional methods known to persons skilled in the art.

The subject of the invention is most particularly a method as defined above, characterized in that the alkylation reaction is accompanied by an enolization reaction of the keto functional group at the 17-position. The enolization reaction is carried out according to standard conditions known to persons skilled in the art. It is carried out in particular by the action of an additional equivalent of a Grignard reagent.

The subject of the invention is most particularly a method as defined above, characterized in that the compounds of formulae (III'a) and (III'b) are treated with a silylating agent in the presence of a base so as to obtain the mixture of silylated enols of formulae (IVa) and (IVb):

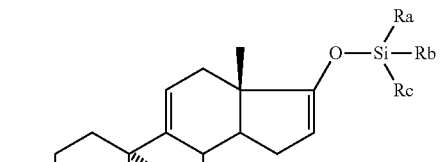

IVa

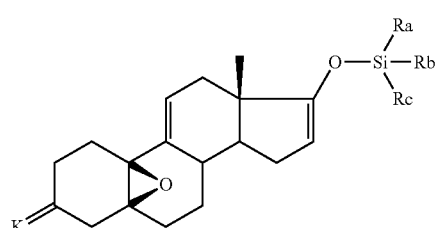

IVb in which, Ra, Rb and Rc, which are identical or different, represent an alkyl radical containing from 1 to 4 carbon atoms, or a phenyl radical,
which is reacted with an organocuprate derivative as defined above, the bonding taking place on the phenyl, so as to obtain the compounds of formulae (IV'a) and (IV'b) which are either isolated or used as such in the next step:

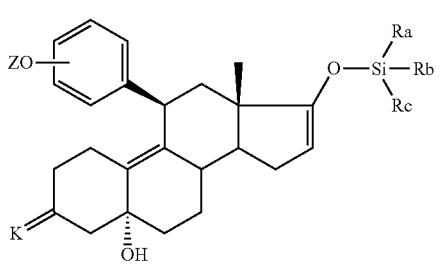

IV'a

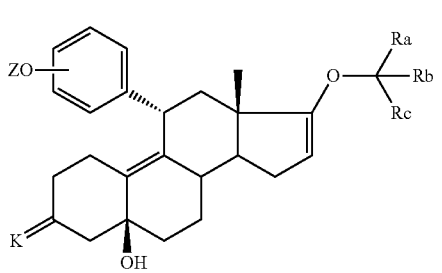

IV'b said products then being deprotected so as to obtain the compounds of formulae (V'a), (V'b), (V'c) as defined above.

The subject of the invention is most particularly a method as defined above, characterized in that the compound of formula (III'b) is treated with a silylating agent in the presence of a base so as to obtain the silylated enol of formula (IVb):

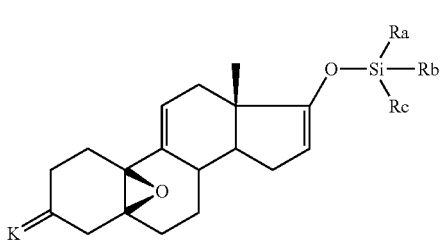

IVb in which Ra, Rb and Rc, which are identical or different, represent an alkyl radical containing from 1 to 4 carbon atoms, or a phenyl radical, which is reacted with an organocuprate derivative as defined above, the bonding taking place on the phenyl, so as to obtain the compound of formula (IV'b) which is either isolated or used as such in the next step:

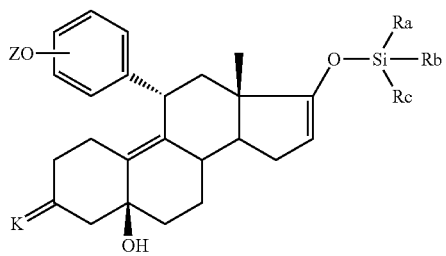

said product then being deprotected so as to obtain the compounds of formulae (V'b), (V'c) as defined above.

As silylating agent, there may be mentioned all the agents capable of silylating enols or enolates known to persons skilled in the art and cited in the monograph Van Look, G.; Simchen, G.; Heberle, J., Silylating Agents; Fluka Chimica, Fluka Chemie AG; Buchs, Switzerland, 1995. It may preferably be a chlorosilane such as trimethylchlorosilane.

This silylation reaction is generally carried out in the presence of a strong base such as Li-HMDS ((Me$_3$Si)$_2$N—Li), or LDA ((iPr)$_2$N—Li).

The solvents used are known to persons skilled in the art for this type of reaction. Protic or enolizable solvents should be avoided. Preferably, the silylation reaction will be carried out with ClSiMe$_3$ in the presence of LDA or Li-HMDS in a mixture of THF and solvents such as pentane, hexanes, cyclohexane, heptane and toluene.

The alkylation reaction is carried out by coupling of the organometallic compound of formula R$_5$MgHal or R$_5$Li with the silylated derivatives of formulae (IVb) and/or (IVa) according to standard conditions known to persons skilled in the art.

The subject of the invention is more particularly a method as defined above, characterized in that the silylated derivative is a trimethylsilyl derivative which makes it possible to obtain the silylated enols of formulae (IVb) and/or (IVa) in which Ra, Rb and Rc are identical and represent a methyl.

The subject of the invention is more particularly a method as defined above, characterized in that =K represents a keto functional group protected in the form of a cyclic ketal, such as 3,3-ethylenedioxy.

The subject of the invention is more particularly a method as defined above, characterized in that (ZO—) is at the para position and Z represents a group R$_4$, with n equal to 2.

The subject of the invention is more particularly a method as defined above, characterized in that R$_1$ and R$_2$ are identical and represent a linear alkyl group, such as the methyl or ethyl radicals.

The subject of the invention is most particularly a method as defined above, characterized in that (ZO—) is at the meta or para position, and Z represents a linear alkyl radical such as the methyl radical.

The subject of the invention is also a method for preparing, as defined above, compounds of formula (I) as defined above in which A represents a group CH—X and Z represents a group R$_4$, comprising the following steps:

a) a compound of formula (II):

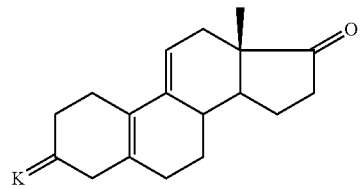

wherein =K representing a keto functional group protected in particular in ketal, thioketal or mixed ketal form, is subjected to the action of an agent reducing the keto at the 17-position so as to obtain a compound of formula (VII):

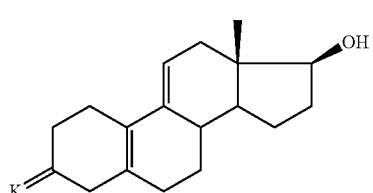

b) the compound of formula (VII) is treated with a halogenating agent so as to obtain a compound of formula (VIII):

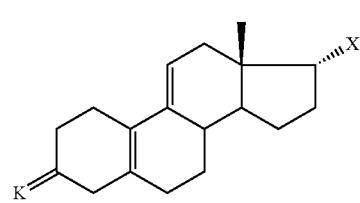

in which X represents a halogen atom, c) the compound of formula (VIII) is subjected to the action of an epoxidation reagent so as to obtain the mixture of the compounds of formulae (III"a) and (III"b):

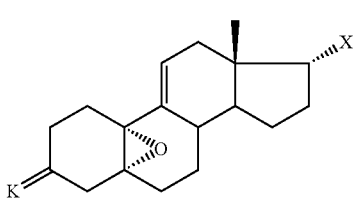

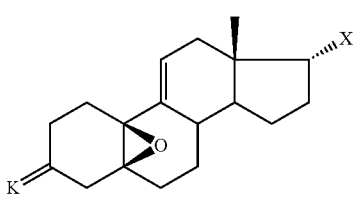

d) the compounds of formulae (III"a) and (III"b) are subjected to an alkylation reaction with an organocuprate derivative derived from an organometallic compound of formula R₅MgHal or R₅Li, Hal being a halogen atom and R₅ representing the group:

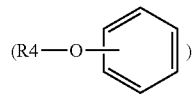

R₄ being as defined above, the bonding taking place on the phenyl, and then to the action of a deprotecting agent so as to obtain the compounds of formulae (V"a), (V"b) and (V"c):

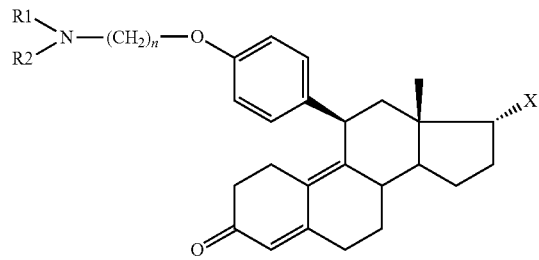

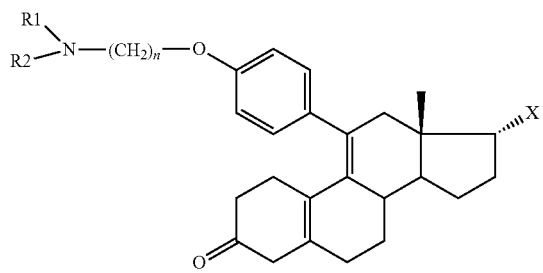

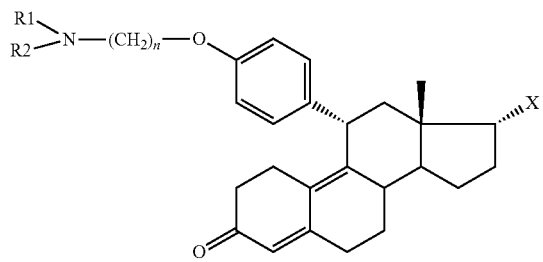

e) the compounds of formulae (V"a), (V"b) and (V"c) are treated with a aromatization agent so as to obtain the mixture of the compounds of formulae (VI") and (I) in which A represents a group CH—X and Z represents a group R₄,

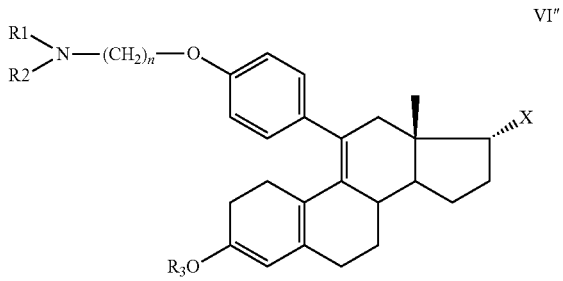

which continue to undergo aromatization so as to obtain the compound of formula (I) as defined above, f) where appropriate, the product obtained in step e is deprotected so as to obtain a compound of formula (I) in which A represents a group CH—X, Z represents a group R₄, and R₃ represents a hydrogen atom, which is subjected, where appropriate, to salinification and neutralization.

The reduction of the 17-keto to an alcohol is carried out according to standard methods, in particular by the action of an alkali metal borohydride such as sodium borohydride in methanol or ethanol or by the action of lithium aluminum hydride in THF. This reaction makes it possible to obtain in particular the alcohol at the 17 beta-position.

The halogenation reaction which follows is carried out in particular with reagents such as $XSO_2C_4F_9$ in the presence of a hindered base such as DBU (diazabicycloundecene), X is preferably fluorine. Other methods known to persons skilled in the art may also be used.

The halogenation reaction may be carried out in particular in the presence of perfluorobutanesulfonyl fluoride, hydrofluoric acid/triethylamine complex ($(HF)_3$/TEA) and DBU.

The alkylation reaction with an organocuprate derivative derived from an organometallic compound R₅MgHal or R₅Li, Hal and R₅ being as defined above, is carried out according to standard methods known to persons skilled in the art.

The aromatization reaction followed by the saponification reaction is carried out according to standard methods as described in European patent 0097572. This aromatization may be preferably carried out in the presence of acetyl bromide and acetic anhydride.

Where appropriate, the deprotection of the formed acetyl group is carried out in general in the presence of a strong base, such as sodium hydroxide or potassium hydroxide, in an alcohol, such as methanol or ethanol.

The salinification and neutralization reactions are carried out by standard methods known to persons skilled in the art.

The subject of the invention is more particularly a method as defined above, characterized in that =K represents a keto functional group protected in cyclic ketal form, such as 3,3-ethylenedioxy.

The subject of the invention is more particularly a method as defined above, characterized in that X represents a fluorine atom.

The subject of the invention is most particularly a method as defined above, characterized in that R₁ and R₂ taken together with the nitrogen atom to which they are attached form a group:

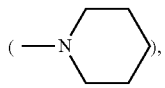

and wherein n is equal to 2.

The compounds of formula (II) are compounds which are known or easily accessible to persons skilled in the art. In particular, the compounds of formula (II) in which =K is a 3,3-ethylenedioxy group are described in the article Crocq, V. et al.; Org. Process. Res. Dev. 1997, 1, 2.

The compounds of formulae (IIIa) and (IIIb) are known compounds. In particular, the compounds of formulae (IIIa) and (IIIb) in which =K is a 3,3-ethylenedioxy group and A represents a keto functional group, are described in the article Larkin, J. P. et al.; Org. Process. Res. Dev. 2002, 6, 20.

The subject of the invention is also, as novel intermediate products, the compound of general formula (IV'b) as defined above and in which Ra, Rb and Rc are identical and represent a methyl, the compound of general formula (VI') as defined above and in which $R_3$ represents an acyl group.

The subject of the invention is more particularly, as novel intermediate products, the compound of general formula (IV'b) as defined above in which (ZO—) is at the para position, the compound of general formula (VI') as defined above in which (ZO—) is at the para position.

The subject of the invention is also, as novel intermediate compounds, the compound of general formula (VIII) in which =K represents 3,3-ethylenedioxy, n is equal to 2, and X represents a fluorine atom, the compounds of general formulae (III"a) and (III"b) in which =K represents 3,3-ethylenedioxy, n is equal to 2, and X represents a fluorine atom, the compounds of general formulae (V"a), (V"b) and (V"c) in which X represents a fluorine atom, n is equal to 2, and $R_1$ and $R_2$ taken together with the nitrogen atom to which they are attached form a group

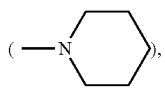

the compound of general formula (VI") in which $R_3$ represents an acyl group, X represents a fluorine atom, n is equal to 2, and $R_1$ and $R_2$ taken together with the nitrogen atom to which they are attached form a group

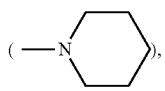

the compound of general formula (I) in which $R_3$ represents an acyl group, X represents a fluorine atom, n is equal to 2, and $R_1$ and $R_2$ taken together with the nitrogen atom to which they are attached form a group

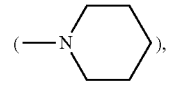

as defined above.

This invention is further illustrated by the following examples which are provided for illustration purposes and in no way limit the scope of the present invention.

EXAMPLES

Example 1

11β-(4-(2-(diethylamino)ethoxy)phenyl)estra-1,3,5 (10)-trien-3-ol-17-one hydrochloride Preparation 1: 4-(2-(diethylamino)ethoxy)phenyl-magnesium bromide was prepared as follows. Initially, about 25 ml solution of 4-(2-(diethylamino) ethoxy)-benzene bromide (74 g; MW=272.2) dissolved in 250 ml of THF was added to magnesium (turnings; MW=24.3; 7.5 g; 1.13 eq.) at around 20° C., with stirring. The mixture was stirred at around 60° C. until the Grignard reagent (exothermic; gray color) was obtained. The remainder of the solution was then carefully added over about 60 min at around 58° C., and the suspension was stirred for 60 min at the same temperature, and then allowed to cool. The concentration of the magnesium compound in solution was about 1.0 M.

Step a: 3,3-ethylenedioxy-5(10)-epoxyestr-9(11)-ene-17-one (about 2/1 mixture of 5(10)-alpha and 5(10)-beta isomers)

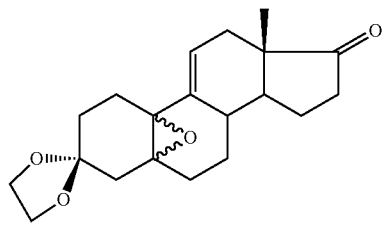

3,3-Ethylenedioxyestra-5(10),9(11)-diene-17-one (50 g; M: 314.4; 0.159 mol), hexachloroacetone (98%; 2.5 ml; 0.1 eq.), pyridine (0.25 ml), hydrogen peroxide at 50% (about 18 M; 15 ml; 1.7 eq) and dichloromethane (250 ml) were vigorously stirred for 18 h at 20-25° C. After reduction in the presence of aqueous sodium thiosulfate, washes (water) and extractions (dichloromethane), the organic phase was concentrated to a total volume of about 150 ml. Next, the dichloromethane was replaced with isopropyl ether by continuous distillation at constant volume, until the internal temperature reached 68° C. The mixture was cooled to around 20° C.—a spontaneous precipitation of the mixture of epoxides was observed. The suspension was cooled and then stirred for 1 h at 0° C., and the product was filtered, and dried under vacuum for 18 h at around 40° C. (44.6 g white solid; yield: 84.9%; HPLC purity: 97%; about 67/33 alpha/beta mixture): $C_{20}H_{26}O_4$; MW: 330.4.

The alpha-epoxide was obtained in pure state (white solid) by crystallization from acetonitrile or ethyl acetate: m.p.: 154° C.; [α]$_D$: +133±2.5 (c=1% in chloroform).

The beta-epoxide was obtained in pure state (white solid) by chromatography (eluent system: heptane 50, ethyl acetate 50, pyridine 0.1): m.p.: 143° C., and it was recrystallized from a mixture of ethyl acetate and isopropyl ether: m.p.: 162-163° C.; [α]$_D$: +101.5±2 (c=1% in chloroform); IR (CHCl$_3$, cm$^{-1}$): 1735, 1640; $^1$H NMR (CDCl$_3$, ppm): 0.86 (s, 3H); 3.92 (m, 4H); 5.86 (m, 1H).

Step b: Silylated enol ether: 3,3-ethylenedioxy-5,10-epoxy-17-trimethylsilyloxyestra-9(11),16(17)-diene (about 2/1 mixture of 5,10-alpha and 5,10-beta isomers)

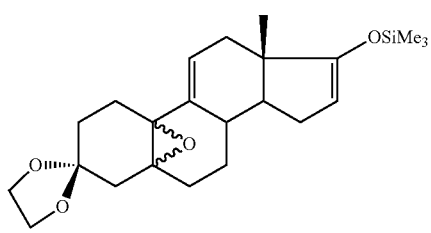

n-Butyllithium (solution at 17% in cyclohexane; 68 g; 1.2 eq.) was added over 30 min to a stirred solution of diisopropylamine (M: 101.2; d: 0.714; 30 ml; 1.4 eq.) in anhydrous THF (100 ml), at –10° C. The lithium diisopropylamine solution thus obtained was added over 30 min at around 0° C. to a solution of epoxide prepared in step A (50 g; 0.151 mol) in THF (150 ml), and the mixture was stirred for 5 min at around 0° C.

Trimethylchlorosilane (M: 108.6; d: 0.856; 27 ml; 1.4 eq.) was added over 15 min at 0° C., and the mixture was stirred for 1 h at around 0° C. Methanol (M: 32; d: 0.792; 5 ml; 0.8 eq.) was added at around 0° C. and the medium was stirred for 30 min at around 10° C. and then poured into the stirred mixture of sodium dihydrogen phosphate dihydrate (M: 156; 26 g; 1.1 eq.), water and toluene. After decantation and washing with water, the toluenic phase was dried over sodium sulfate and concentrated under vacuum to a final volume of about 100 ml. The silylated enol ether was used in this form in the next step, but an isolation by dry extract is possible: C$_{23}$H$_{34}$O$_4$Si; MW: 402.6.

The alpha-epoxide (amorphous solid, m.p.<40° C.) was obtained in pure state by the same procedure, but starting with pure alpha-epoxide, which is obtained in accordance with the procedures as set forth in step A:

IR (CHCl$_3$, cm$^{-1}$): 1621, 1254, 849

$^1$H NMR (CDCl$_3$, ppm): 0.19 (s, 9H); 0.80 (s, 3H); 3.85-4.00 (m, 4H); 4.47 (dd, J=1.5 and 1 Hz, 1H); 6.03 (m, 1H)

MS (m/z): 402 (M$^+$), 387 (M$^+$-CH$_3$), 99.

The beta-epoxide (oil) was obtained in pure state by the same procedure, but starting with pure beta-epoxide, which is obtained in accordance with the procedures as set forth in step A: $^1$H NMR (CDCl$_3$, ppm): 0.19 (s, 9H); 0.78 (s, 3H); 1.12 (m, 1H); 2.34 (d, J=15 Hz, 1H); 3.90 (m, 4H); 4.48 (m, 1H); 5.84 (m, 1H).

Step c: Mixture of 11-(4-(2-(diethylamino)ethoxy)-phenyl)estra-5(10),9(11)-diene-3,17-dione and 11-alpha-(4-(2-(diethylamino)ethoxy)phenyl)estra-4,9-diene-3,17-dione

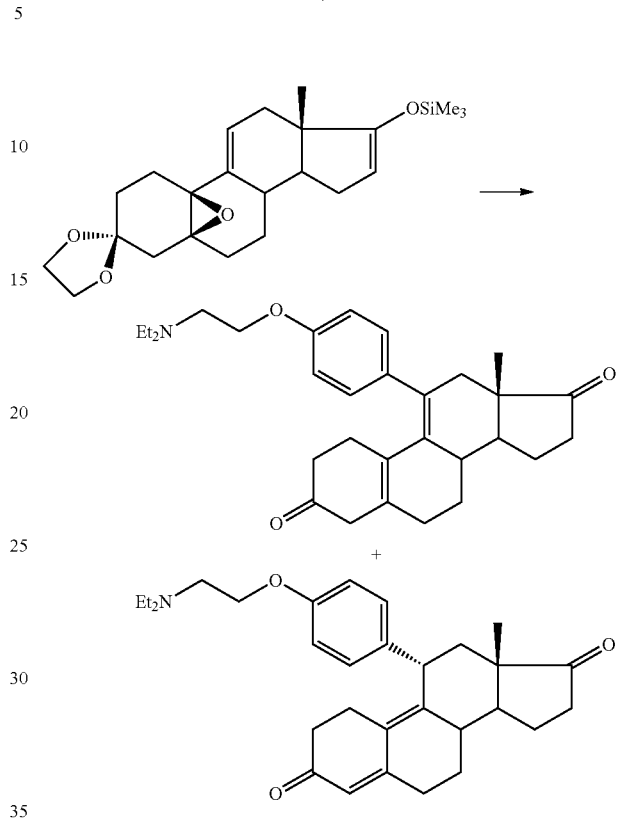

Copper (I) chloride (MW=99.0; 509 mg; 0.17 eq.) was added at around 20° C. to a solution of silylated enol ether (pure beta isomer) as prepared above (step B) (12.2 g; 30.3 mmol) in THF (30 ml). The medium was cooled to around –3° C. and the solution of the magnesium compound as described above (preparation 1) (61 ml; about 1 M; 2 eq) was added while maintaining the temperature at –3° C. The medium was stirred for about 3 h at around 20° C., and then poured into a mixture of ammonium chloride (50 g) in water (200 ml). The medium was extracted with dichloromethane. The organic phase was then washed with water and concentrated under vacuum. Dichloromethane (80 ml) and water (30 ml) were added. The mixture was cooled at 0-5° C. and hydrochloric acid at 36% (12 ml; 4.75 eq.) was added over 20 min. The biphasic medium was vigorously stirred for 2 h at about 0° C., and then diluted with water (50 ml). The organic phase was separated by decantation and washed with water. The amine-containing by-products were removed in the acidic aqueous phase while the hydrochloric acid salts of the enones remain in dichloromethane. The organic phase was neutralized by washing with an aqueous sodium hydrogen carbonate solution (50 ml), washed with water, dried over sodium sulfate and then concentrated under vacuum. The residue (11 g) is chromatographed on a silica column (eluent: n-heptane 50, ethyl acetate 45, triethylamine 5). The fractions were concentrated to dryness to obtain:—800 mg of 11-(4-(2-(diethylamino)-ethoxy)phenyl)estra-5(10),9(11)-diene-3,17-dione: C$_{30}$H$_{39}$NO$_3$; MW: 461.6;

IR (CHCl$_3$, cm$^{-1}$): 1733, 1712, 1607, 1568, 1508;

$^1$H NMR (CDCl$_3$, ppm): 1.03 (s, 3H); 1.12 (t, J=7 Hz, 6H) and 2.72 (q, J=7 Hz, 4H); 2.94 (t, J=6 Hz, 2H); 4.09 (t, J=6 Hz, 2H); 6.82 and 7.07 (m, 4H); from 1.0 to 2.9 (m, 18H);

MS (EI, m/z): 461 (M$^+$); and 444 mg of 11-alpha-(4-(2-(diethylamino)ethoxy)phenyl)-estra-4,9-diene-3,17-dione: C$_{30}$H$_{39}$NO$_3$; MW: 461.6:

$^1$H NMR (CDCl$_3$, ppm): 1.02 (s, 3H); 1.12 (t, J=7 Hz, 6H) and 2.69 (q, J=7 Hz, 4H); 2.91 (t, J=7 Hz, 2H); 4.05 (m, 3H); 5.72 (s, 1H); 6.79 and 6.95 (m, 4H); from 1.0 to 2.8 (m, 16H);

MS (ESP, m/z): 426 (MH$^+$).

Step c: Mixture of 11-beta-(4-(2-(diethylamino) ethoxy)-phenyl)estra-4,9-diene-3,17-dione, 11-(4-(2-(diethylamino)ethoxy)phenyl)estra-5(10),9(11)-diene-3,17-dione and 11-alpha-(4-(2-(diethylamino) ethoxy)phenyl)-estra-4,9-diene-3,17-dione.

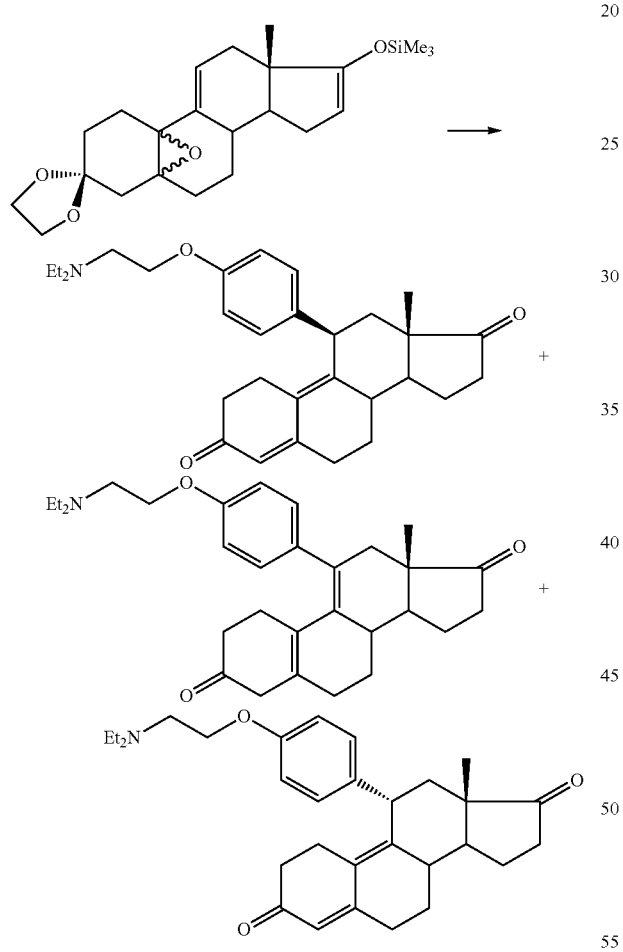

Copper (I) chloride (MW=99.0; 2.24 g; 0.25 eq.) was added at around 20° C. to a solution of the magnesium compound as described above (preparation 1) (182 ml; about 1 M; 2.0 eq). The medium was stirred for 15 min at around 20° C. and then a solution of silylated enol ether (about 2/1 beta-alpha mixture) as prepared above (step B) (36.5 g; 90.7 mmol) was introduced with THF (120 ml). The medium was stirred for about 1 h at around 20° C., and then poured into a mixture of ammonium chloride (150 g) in water (600 ml). The medium was extracted with dichloromethane. The organic phase was then washed with water and concentrated under vacuum. Dichloromethane (150 ml) and water (75 ml) were added. The mixture was cooled to 0-5° C. and hydrochloric acid at 36% (45 ml; 6 eq.) was added over 45 min. The biphasic medium was vigorously stirred for 1.5 h at around 0° C., and then diluted with water (150 ml). The organic phase was separated by decantation and washed with water. The organic phase was neutralized by washing with a saturated aqueous sodium hydrogen carbonate solution (150 ml), washed with water, dried over sodium sulfate and then concentrated under vacuum.

The product thus obtained was an orange-colored resin: 36 g; yield: 86%: C$_{30}$H$_{39}$NO$_3$; MW: 461.6.

11-Beta-(4-(2-(diethylamino)ethoxy)phenyl)estra-4,9-diene-3,17-dione was isolated by crystallization from isopropyl ether (which crystallization was all the more efficient as the alpha/beta ratio in the initial mixture of epoxides was high).

11-(4-(2-(Diethylamino)ethoxy)phenyl)estra-5(10),9 (11)-diene-3,17-dione and 11-alpha-(4-(2-(diethylamino) ethoxy)phenyl)estra-4,9-diene-3,17-dione was isolated by chromatography on silica as described in the preceding example.

11-Beta-(4-(2-(diethylamino)ethoxy)phenyl)estra-4,9-diene-3,17-dione: m.p.=188° C.;

IR (CHCl$_3$, cm$^{-1}$): 1735, 1658, 1609, 1581, 1509;

$^1$H NMR (CDCl$_3$, ppm): 0.56 (s, 3H); 1.06 (t, J=7 Hz, 6H) and 2.63 (q, J=7 Hz, 4H); 2.85 (t, J=6 Hz, 2H); 4.01 (t, J=6 Hz, 2H); 4.38 (dl, J=7 Hz, 1H); 5.80 (bs, 1H); 6.82 and 7.07 (AA'BB', 4H); from 1.4 to 2.9 (m, 16H);

MS (EI, m/z): 461 (M$^+$).

Step d: Mixture of 3-acetyl-11-beta-(4-(2-(diethylamino)ethoxy)phenyl)estra-1,3,5(10)-trien-17-one hydrochloride and 3-acetyl-11-(4-(2-(diethylamino) ethoxy)phenyl)estra-3,5(10),9(11)-trien-17-one hydrochloride.

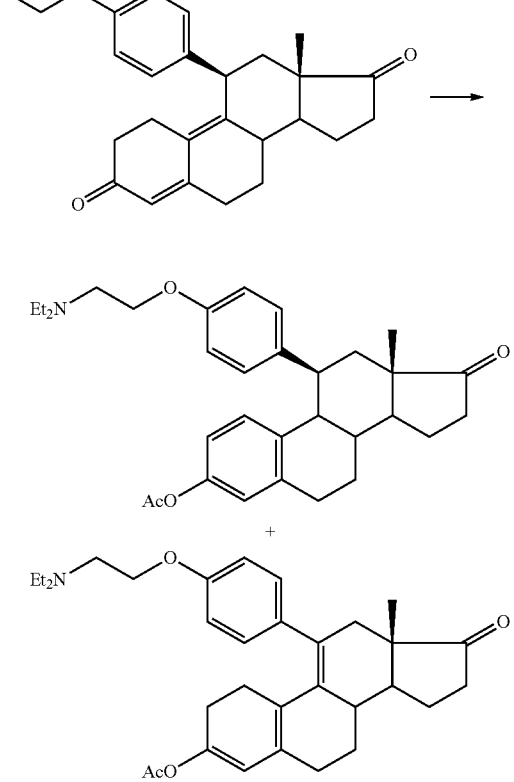

To a solution of 11-beta-(4-(2-(diethylamino)ethoxy)-phenyl)estra-4,9-diene-3,17-dione prepared in step c (10 g; 21.6 mmol) in dichloromethane (40 ml) were added acetic anhydride (MW=102.1; d=1.09; 6.1 ml; 3 eq.) and, and over 5 min, acetylbromide (MW=123.0; d=1.66; 6.1 ml; 3.8 eq.), at 20-25° C. The brown solution was stirred for 1 h at 20-25° C. The solution was poured over in about 30 min into a suspension of sodium hydrogen carbonate (24.4 g) in water (100 ml) at around 20° C. (emission of carbon dioxide). The mixture was vigorously stirred for 30 min at around 20° C., and then the organic phase was separated by decantation, washed with water, dried over sodium sulfate and then concentrated to dryness under vacuum. The residue (18 g) was chromatographed on a silica column (eluent: cyclohexane/ethyl acetate/triethylamine 75/20/5). Each fraction was concentrated to dryness separately, taken up in dichloromethane and acidified to pH=1 with 1 N aqueous hydrochloric acid. The organic phase was separated by decantation, dried over sodium sulfate and concentrated to dryness. The least polar fraction thus acidified gave 3-acetyl-11-(4-(2-(diethylamino)ethoxy)-phenyl)estra-3,5(10),9(11)-trien-17-one hydrochloride (1.3 g; yellow solid; 10%): $C_{32}H_{42}NO_4Cl$; MW: 540.1.

IR (CHCl$_3$, cm$^{-1}$): ν 1736, 1664, 1606, 1570, 1507;

$^1$H NMR (CDCl$_3$, ppm): δ 1.02 (s, 3H); 1.47 (td, J=7 Hz, 6H) and 3.27 (m, 4H); 2.10 (s, 3H); 3.47 (m, 2H); 4.51 (m, 2H); 5.52 (d, J=1.5 Hz, 1H); 6.79 and 7.12 (AA'BB', 4H); 12.4 (bs, 1H, active); from 1.0 to 2.6 (m, 16H);

MS (EI; m/z): 503 (M$^+$); 461; 100; 86; 38 and 36 (HCl).

The acidified more polar fraction gave 3-acetyl-11-beta-(4-(2-(diethylamino)ethoxy)phenyl)estra-1,3,5(10)-trien-17-one hydrochloride (6.09 g; white solid; 52%): $C_{32}H_{42}NO_4Cl$; MW: 540.1.

IR (CHCl$_3$, cm$^{-1}$): ν 1734, 1610, 1582, 1512, 1494;

$^1$H NMR (CDCl$_3$, ppm): δ 0.45 (s, 3H); 1.43 (t, J=7 Hz, 6H) and 3.22 (m, 4H); 2.25 (s, 3H); 3.39 (m, 2H); 4.40 (m, 2H); 4.04 (d, J=4.5 Hz, 1H); 6.63 and 6.99 (AA'BB', 4H); 6.65 (dd, J=8.5 and 1.5 Hz, 1H); 6.86 (d, J=1.5 Hz, 1H); 6.94 (d, J=8.5 Hz, 1H); 12.3 (bs, 1H, active); from 0.85 to 3.5 (m, 13H);

MS (EI; m/z): 503 (M$^+$), 86, 38 and 36 (HCl).

Step e: 3-Acetyl-11-beta-(4-(2-(diethylamino)ethoxy)-phenyl)estra-3,5(10),9(11)-trien-17-one

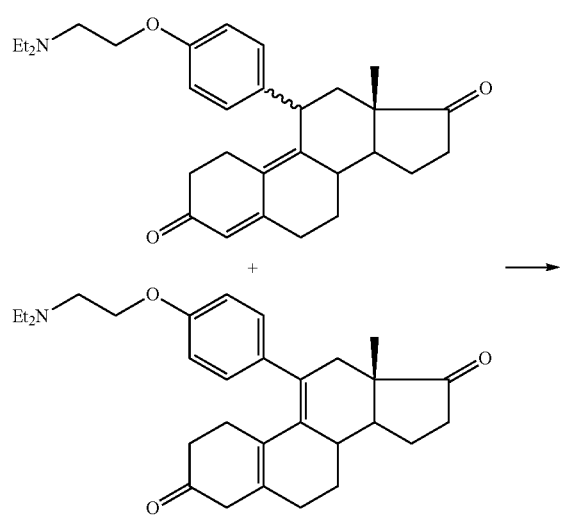

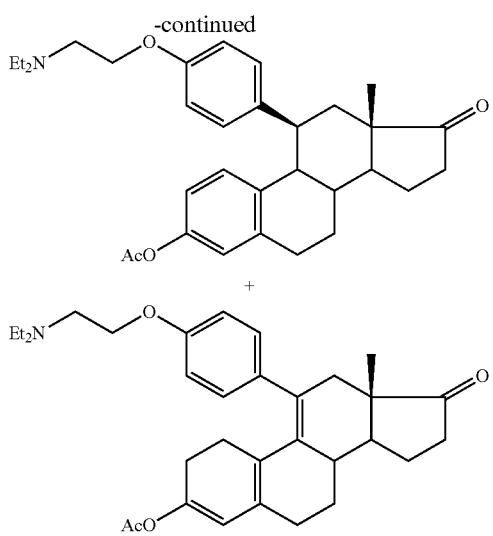

To the solution of enones prepared in step c (35 g; 75.8 mmol) in dichloromethane (250 ml) were added acetic anhydride (MW=102.1; d=1.09; 7.1 ml; 1 eq.) and, over a period of about 20 min, acetylbromide (MW=123.0; d=1.66; 14 ml; 2.5 eq.), at 20-25° C. (exothermic addition). The brown solution thus obtained was stirred for 5 h at 20-25° C. The disappearance of the 3-acetyltriene was monitored by HPLC (Hypersil DBS 3 microns CN, 150×4.6 mm; eluent: water containing 0.1% of trifluoroacetic acid, acetone, methanol 65/30/5; UV 210 nm). The solution was poured over in about 30 nm into a suspension of sodium hydrogen carbonate (93 g) in water (350 ml) at around 20° C. (emission of carbon dioxide). The mixture was vigorously stirred overnight at around 20° C., and then the organic phase was separated by decantation, washed with 1N sodium hydroxide (175 ml) and water and then concentrated to a final volume of 100 ml. Dichloromethane was replaced with methanol at constant volume by distillation under gradual vacuum at about 40° C. The product was stored in solution in methanol. $C_{32}H_{41}NO_4$; MW: 503.7.

Step f: 11-Beta-(4-(2-(diethylamino)ethoxy)phenyl)estra-1,3,5(10)-trien-3-ol-17-one hydrochloride A solution of potassium hydroxide (MW=56.0; 6.3 g; 1.5 eq.) in methanol (70 ml) was added over in about 10 min, at around 0° C., to the 3-acetyl-11-beta-(4-(2-(diethylamino)ethoxy)phenyl)estra-3,5(10),9(11)-trien-17-one solution in methanol obtained in step e. The medium was stirred for 2 h at 0-5° C., and then poured into water (175 ml) and dichloromethane (175 ml). The organic phase was separated by decantation and washed with water. Water (175 ml) and hydrochloric acid at 36% (16 ml; 2.5 eq.) were added and the medium was stirred for about 5 min while monitoring the pH (<2). The organic phase was separated by decantation, dried over sodium sulfate, filtered and concentrated until a final volume of 175 ml was obtained. The medium was then distillated while the volume was kept constant by gradual introduction of 2-butanone. The expected product crystallized spontaneously. The temperature at the end of the exchange was about 78° C. The medium was stirred, while allowing it to cool in about 1 h, and then the stirring continued for 1 h at about 20° C. The product was filtered, washed with 2-butanone and then dried under vacuum at around 70° C. (24.4 g beige solid; m.p.=179° C.; yield: 64.6%): $C_{30}H_{40}ClNO_3$; MW: 498.1;

IR (CHCl$_3$, cm$^{-1}$): v 3601, 2456, 1733, 1610, 1584, 1511;
$^1$H NMR (CDCl$_3$, ppm): δ 0.42 (s, 3H), 1.31 (m, 6H), 3.16 (m, 4H), 3.31 (m, 2H), 3.96 (bt, 1H), 4.17 (m, 2H), 6.51 (m, 1H), 6.68 (m, 1H), 6.73 (m, 1H), 6.51 and 6.95 (AA'BB', 4H), 11.36 (bs; 1H);
MS (EI; m/z): 461 (M$^+$), 446, 362, 86, 38 and 36 (HCl).

Example 2

11β-(4-(2-(Diethylamino)ethoxy)phenyl)estra-1,3,5 (10)-trien-3-β1-17-one hydrochloride Step c: Mixture of 11-beta-(4-(2-(diethylamino) ethoxy)-phenyl)estra-4,9-diene-3,17-dione, 11-(4-(2-(diethylamino)ethoxy)phenyl)estra-5(10),9(11)-diene-3,17-dione and 11-alpha-(4-(2-(diethylamino) ethoxy)phenyl)-estra-4,9-diene-3,17-dione.

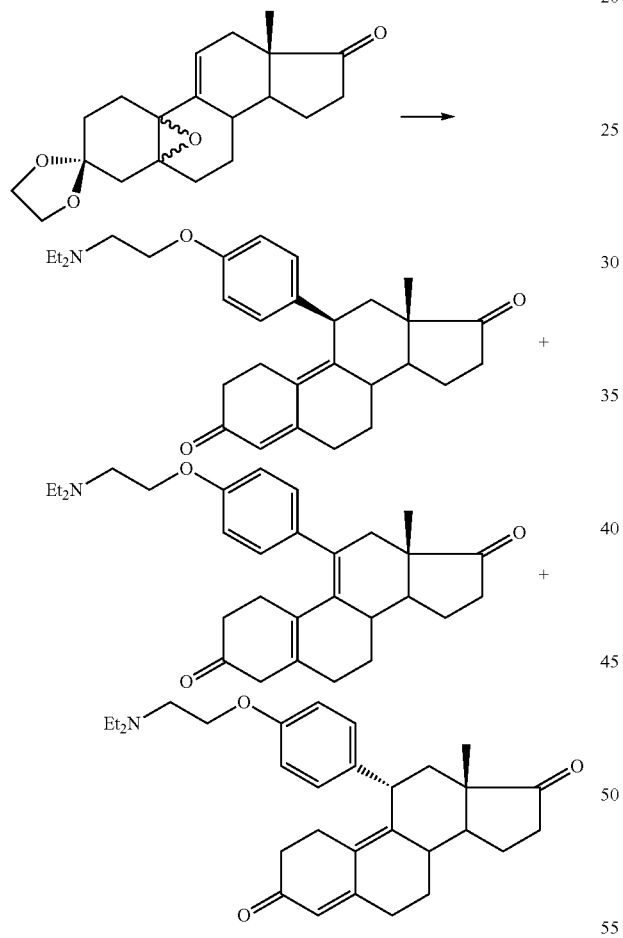

Initially, about 25 ml solution of 4-(2-(diethylamino)-ethoxy)benzene bromide (123.6 g; MW=272.2; 3 eq.) in THF (250 ml) was added to magnesium (turnings; MW=24.3; 11.8 g; 3.2 eq.) at around 20° C., with stirring. The mixture was stirred at around 60° C. until the Grignard reagent was formed (exothermic; gray color). The remainder of the solution was then carefully added over about 60 min at around 58° C., and the suspension was stirred for 60 min at the same temperature, and then allowed to cool. Copper (I) chloride (MW=99.0; 3.75 g; 0.25 eq.) was added at around 20° C. and the suspension obtained was stirred for about 15 min at around 20° C.

The mixture of epoxides (step A) (50 g; 0.151 mol) solubilized in THF (300 ml) was added over 30 min at around 20° C. to the suspension. The mixture was stirred for 1 h at around 20° C., and then poured into a mixture of ammonium chloride (125 g) in water (600 ml). The medium was extracted with dichloromethane. The organic phase was then washed with water and concentrated under vacuum. Dichloromethane (600 ml) and water (125 ml) were added. The mixture was cooled at 0-5° C. and hydrochloric acid at 36% (100 ml; 7.7 eq.) was added over 20 min. The biphasic medium was vigorously stirred for 2 h at around 0° C., and then diluted with water (250 ml). The organic phase was separated by decantation and washed with water. The amine-containing by-products were removed in the acidic aqueous phase while the hydrochloric acid salts of the enones remained in dichloromethane. The organic phase was neutralized by washing with an aqueous sodium hydrogen carbonate solution (25 g; 2 eq.), washed with water, dried over sodium sulfate and then concentrated under vacuum. The product thus obtained was in semicrystalline form: 65.3 g; yield: 93.5% (from the epoxide 2): C$_{30}$H$_{39}$NO$_3$; MW: 461.6.

Step e: 3-Acetyl-11-beta-(4-(2-(diethylamino) ethoxy)-phenyl)estra-3,5(10),9(11)-trien-17-one

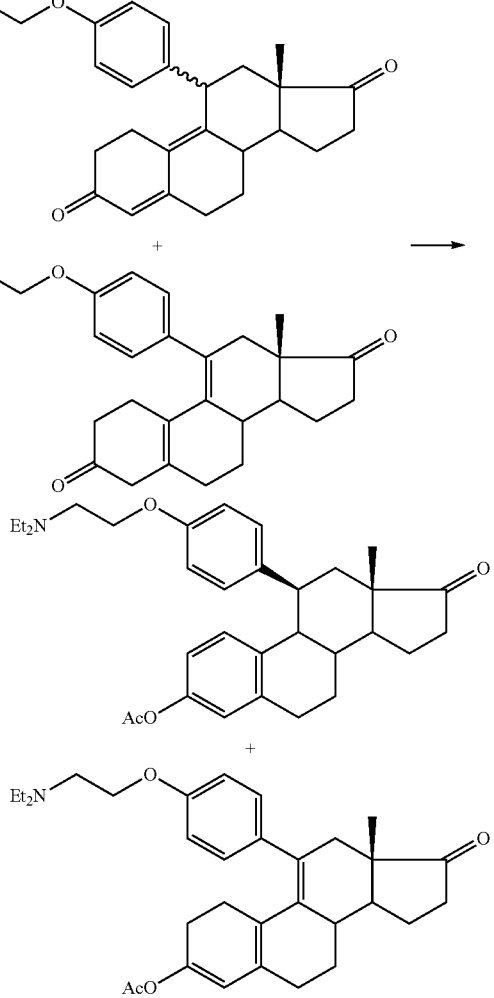

To a solution of enones prepared in step c (65.3 g; 0.141 mol) in dichloromethane (250 ml) were added acetic anhydride (MW=102.1; d=1.09; 14.2 ml; 1.1 eq.) and, over 15 min, acetyl bromide (MW=123.0; d=1.66; 28 ml; 2.7 eq.), at 20-25° C. (exothermic addition). The brown solution was stirred for 5 h at 20-25° C. The disappearance of the 3-acetyl-triene was monitored by HPLC (Hypersil DBS 3 microns CN, 150×4.6 mm; eluent: water containing 0.1% of trifluoroacetic acid, acetone, methanol 65/30/5; UV 210 nm). The solution was poured over a suspension of sodium hydrogen carbonate (127 g) in water (500 ml) at around 20° C. (emission of carbon dioxide) in about 30 min. The mixture was vigorously stirred overnight at around 20° C., and then the organic phase was separated by decantation, washed with 1 N sodium hydroxide (250 ml) and water (3×250 ml) and then concentrated to a final volume of 150 ml. The dichloromethane is replaced with methanol at constant volume by distillation under gradual vacuum at about 40° C. The product was stored in solution in methanol. $C_{32}H_{41}NO_4$; MW: 503.7.

Step f: 11-Beta-(4-(2-(diethylamino)ethoxy)phenyl) estra-1,3,5(10)-trien-3-ol-17-one hydrochloride A solution of potassium hydroxide (MW=56.0; 12.7 g; 1.6 eq.) in methanol (100 ml) was added over 10 min at around 0° C. to the solution of 3-acetyl-11-beta-(4-(2-(diethylamino) ethoxy)phenyl)estra-3,5(10),9(11)-trien-17-one in methanol obtained in step e. The medium was stirred for 1.5 h at 0-5° C., and then poured into water (250 ml) and dichloromethane (250 ml). The organic phase was washed with water. The medium was acidified by adding water and hydrochloric acid at 36% (26 ml; 2.2 eq.) and stirred for about 5 min while monitoring the pH (<2). The organic phase was separated by decantation, dried over sodium sulfate, filtered and concentrated until a final volume of 300 ml was obtained. The medium was then distilled while maintaining the volume constant by gradual introduction of 2-butanone. The expected product crystallized spontaneously. The temperature at the end of the exchange was about 78° C. The medium was stirred, while allowing it to cool over about 1 h, and then for 1 h at around 20° C. The product was filtered, washed with 2-butanone and then dried under vacuum at around 70° C. (48 g beige solid; m.p.=179° C.; yield: 68.3%, HPLC purity: 95%): $C_{30}H_{40}ClNO_3$; MW: 498.1. Same spectral data were observed as those set forth in Example 1, step f.

Example 3

11-Beta-(4-(2-(dimethylamino)ethoxy)phenyl)-estra-1,3,5(10)-trien-3-ol-17-one

Preparation 2:
4-(2-(Diethylamino)ethoxy)phenylmagnesium bromide

A solution of 4-(2-(dimethylamino)ethoxy)benzene bromide (18.3 g; MW=244.1) in THF (90 ml) was added dropwise, with stirring at 35-40° C., to magnesium (turnings; MW=24.3; 2.2 g; 1.2 eq.), after having initiated the reaction with a few drops of dibromoethane, in 10 ml of anhydrous THF. After the end of the introduction, the gray solution obtained was stirred for 90 min at the same temperature, and then allowed to cool. The concentration of the magnesium compound thus formed in solution is about 0.55 M (titer by iodometry).

Step c: 3,3-Ethylenedioxy-11-alpha-(4-(2-(dimethylamino) ethoxy)phenyl)estr-9-en-5-beta-ol-17-one

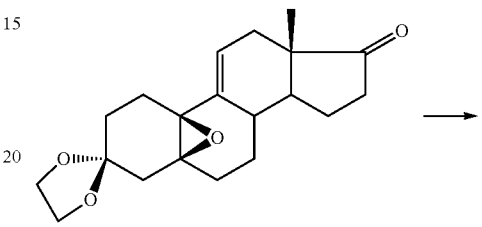

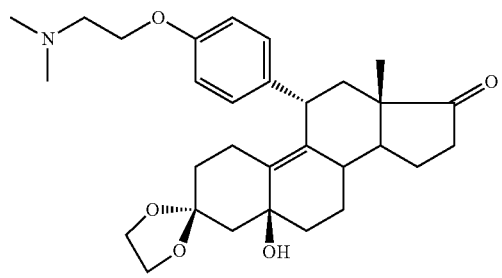

A solution of magnesium compound prepared above (preparation 2) (82.5 ml; 0.55 M; 3 eq.) was added to a suspension of anhydrous copper (I) chloride (MW=99; 0.5 g; 0.33 eq.) in anhydrous THF (20 ml) stirred for 10 min at 20° C. The mixture was cooled in an ice bath. A solution of 3,3-ethylenedioxy-5-beta,10-beta-epoxyestr-9(11)-en-17-one (4.95 g; M: 330.42; 15 mmol) in anhydrous THF (50 ml) was added thereto, with stirring, at around 0° C. and over 20 min. After stirring for 4 h, the mixture was poured over an ice-cold, saturated aqueous ammonium chloride solution, and the product was extracted with ethyl acetate. The organic phase was washed with salt water, dried over sodium sulfate and then concentrated under vacuum. The residue (14 g) was then chromatographed on a silica column (eluent: cyclohexane 40, ethyl acetate 40, triethylamine 20). The fractions were concentrated to dryness so as to obtain:

5.7 g of 3,3-ethylenedioxy-11-alpha-(4-(2-(dimethylamino)ethoxy)phenyl)estr-9-en-5-beta-ol-17-one, yield: 77%, $C_{30}H_{41}NO_5$; MW: 495.6.

By crystallization (dissolution in a small volume of dichloromethane and then addition of isopropyl ether and slight concentration under vacuum), draining and drying at 50° C. under vacuum, there were obtained:

4.24 g of white crystals, m.p.=122° C.

IR ($CHCl_3$, $cm^{-1}$): 3510, 1735, 1609, 1578, 1510.

Step d: 11-Alpha-(4-(2-(dimethylamino)ethoxy)phenyl)-estra-4,9-diene-3,17-dione and 11-(4-(2-(dimethylamino)ethoxy)phenyl)estra-5(10),9(11)-diene-3,17-dione.

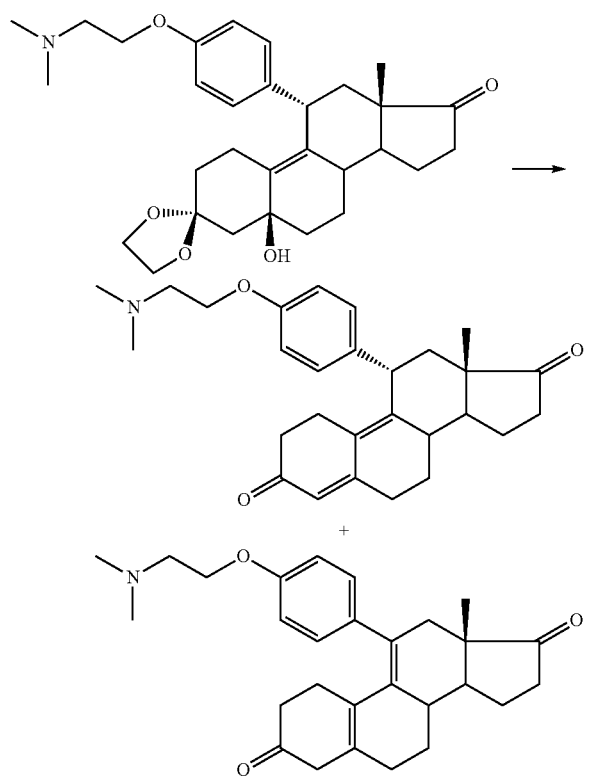

Method a: 2 N hydrochloric acid (1 ml) was slowly added, with stirring, to a solution of 3,3-ethylenedioxy-11-alpha-(4-(2-(dimethylamino)ethoxy)phenyl)estr-9-en-5-beta-ol-17-one prepared in step c (0.55 g; 1.1 mmol) in methanol (6 ml). After stirring for 1 h 30 min, the solution was concentrated under vacuum and the residue was dissolved in water and then made alkaline with a saturated aqueous sodium bicarbonate solution. The product was extracted with ethyl acetate. The organic phase was washed with salt water, dried over sodium sulfate and then concentrated under vacuum. The residue (0.5 g) was chromatographed on a silica column (eluent: cyclohexane 40, ethyl acetate 40, triethylamine 20). The fractions were concentrated to dryness so as to obtain:

0.325 g of 11-(4-(2-(dimethylamino)ethoxy)phenyl)estra-5(10),9(11)-diene-3,17-dione, yield: 67%, $C_{28}H_{35}NO_3$; MW: 433.6.

IR ($CHCl_3$, $cm^{-1}$): 1730, 1705, 1600;

0.025 g of 11-alpha-(4-(2-(dimethylamino)ethoxy)-phenyl)estra-4,9-diene-3,17-dione, identical to the product obtained by method b, yield: 5%, $C_{28}H_{35}NO_3$; MW: 433.6.

Method b: Perchloric acid at 55° C. (2 ml) was slowly added with stirring to a solution of 3,3-ethylenedioxy-11-alpha-(4-(2-(dimethylamino)ethoxy)phenyl)estr-9-en-5-beta-ol-17-one prepared in step c (0.5 g; 1 mmol) in acetic acid (1 ml). After 1 h 45 min of contact, the mixture was slowly poured, while cooling, into a saturated aqueous sodium bicarbonate solution. The product was extracted with ethyl acetate. The organic phase was washed with salt water, dried over sodium sulfate and then concentrated under vacuum. The residue (0.5 g) was chromatographed on a silica column (eluent: cyclohexane 40, ethyl acetate 40, triethylamine 20). The fractions were concentrated to dryness so as to obtain:

0.16 g of 11-alpha-(4-(2-(dimethylamino)ethoxy)phenyl)-estra-4,9-diene-3,17-dione, yield: 36%, $C_{28}H_{35}NO_3$; MW: 433.6.

IR ($CHCl_3$, $cm^{-1}$): 1739, 1652, 1609, 1580, 1510;

$^1$H NMR ($CDCl_3$, ppm): 1.03 (s, 3H); 2.32 (s, 6H); 2.71 (t, J=6 Hz, 2H); 4.03 (t, J=6 Hz, 2H); 4.06 (t, J=9 Hz, 1H); 5.72 (s, 1H); 6.83 and 6.99 (AA'BB', 4H).

Step e: 11-Beta-(4-(2-(dimethylamino)ethoxy)phenyl)-estra-1,3,5(10)-trien-3-ol-17-one

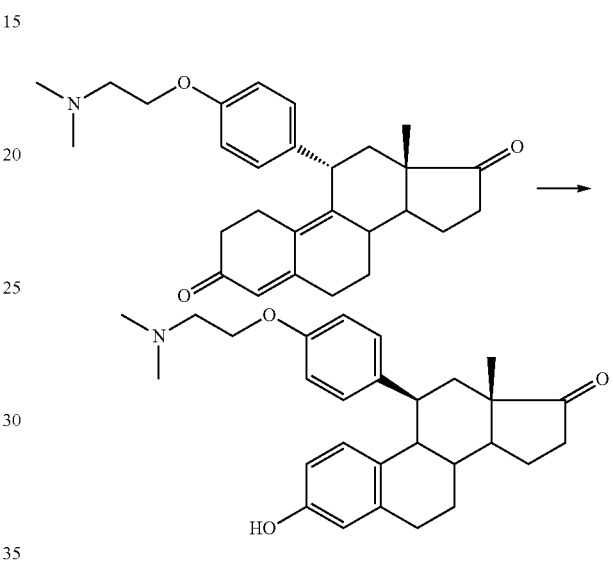

The 11-alpha-(4-(2-(dimethylamino)ethoxy)phenyl)estra-4,9-diene-3,17-dione (0.2 g; 0.46 mmol) prepared in step d was dissolved in dry methylene chloride (2 ml). The solution was cooled to 0° C. and then acetic anhydride (0.2 ml; 2.11 mmol; 4.5 eq.) was added dropwise thereto at this temperature followed by acetyl bromide (0.1 ml; 1.34 mmol; 3 eq.). The solution obtained was stirred at room temperature for 1 h 45 min. It was carefully made alkaline by adding a saturated aqueous sodium bicarbonate solution. The product was extracted with dichloromethane. The organic phase was washed with salt water, dried over sodium sulfate and then concentrated under vacuum. The residue (0.21 g) was dissolved in methanol (5 ml). 2 N sodium hydroxide was added and then the medium was stirred at room temperature for 45 min. The mixture was then acidified with 2 N hydrochloric acid, and then again alkalinized with a saturated aqueous sodium bicarbonate solution. The product was extracted with dichloromethane. The organic phase was washed with salt water, dried over sodium sulfate and then concentrated under vacuum. The residue (0.19 g) was chromatographed on a silica column (eluent: cyclohexane 40, ethyl acetate 40, triethylamine 20). The fractions were concentrated to dryness so as to obtain:

0.13 g of 11-beta-(4-(2-(dimethylamino)ethoxy)phenyl)-estra-1,3,5(10)-trien-3-ol-17-one, yield: 65%, $C_{28}H_{35}NO_3$; MW: 433.6.

IR ($CHCl_3$, $cm^{-1}$): 3595, 1735, 1610, 1580, 1512;

$^1$H NMR ($CDCl_3$, ppm): 0.47 (s, 3H); 2.33 (s, 6H); 3.94 (m, 2H); 3.99 (t, J=4.5 Hz, 1H); 6.37 (dd, J=2.5 and 8.5 Hz, 1H); 6.49 (d, J=2.5 Hz, 1H); 6.77 (d, J=8.5 Hz, 1H); 6.50 and 6.96 (AA'BB', 4H).

Example 4

11-Beta-(4-(2-(1-piperidinyl)ethoxy)phenyl)-17-alpha-fluoroestra-1,3,5(10)-trien-3-ol Step a: Reduction 3,3-ethylenedioxyestra-5(10),9(11)-diene-17-ol

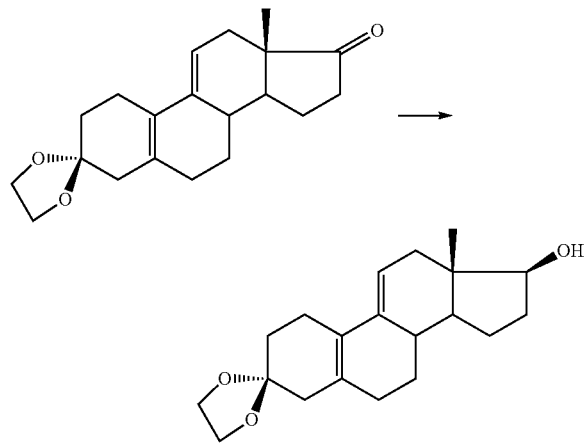

Sodium borohydride (MW=37.8; 18.9 g; 500 mmol) dissolved in 0.5 N sodium hydroxide (100 ml) was introduced over about 5 min at around 2° C. into a suspension of 3,3-ethylenedioxyestra-5(10),9(11)-diene-17-one (MW=314.4; 100 g; 318 mmol) in methanol (1 liter). The medium was stirred for 2 h at around 2° C. and then acetone (100 ml) was introduced over about 15 min at around 5° C. The medium was stirred for 1 h, and poured at around 20° C. into the stirred mixture of water (2 liters), sodium chloride (500 g) and ethyl acetate (400 ml). The medium was separated by decantation and the aqueous phase was re-extracted with ethyl acetate. The combined organic phases were washed with water, dried over sodium sulfate and concentrated at atmospheric pressure at 500 ml. The distillation is continued while the volume is kept constant by gradual introduction of 1,2-dimethoxyethane (DME). The temperature at the end of the exchange is 83° C. The solution was used as it is in the next step, but a dry extract gave the expected product (resin). $C_{20}H_{28}O_3$; MW=316.4.

IR (CHCl$_3$, cm$^{-1}$): ν 3613, 1638.

$^1$H NMR (CDCl$_3$, ppm): δ 0.74 (s, 3H), 2.29 (bs, 2H), 3.78 (t, J=8.5 Hz, 1H), 3.98 (m, 4H), 5.57 (m, 1H), from 0.85 to 2.6 (m, 16H).

Step b: Fluorination 3,3-Ethylenedioxy-17-alpha-fluoroestra-5(10),9(11)-diene

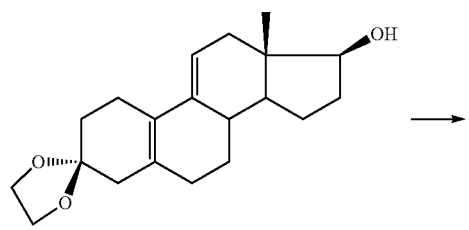

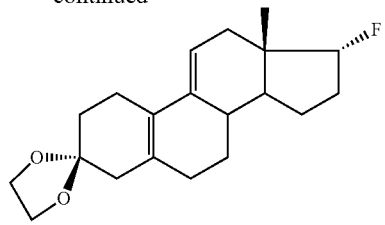

Perfluorobutanesulfonyl fluoride (MW=302.1; 41.4 g; 137 mmol) was introduced over about 5 min at around −10° C. into the solution of 3,3-ethylenedioxyestra-5(10),9(11)-diene-17-ol (MW=316.4; 20 g; 63.2 mmol) in DME (100 ml) obtained in the preceding step. The suspension was cooled to around −40° C. and the 3HF.TEA complex (MW=161.2; 10.2 g; 63.3 mmol) was introduced over about 30 min at this temperature. The medium was stirred for about 15 min at around −40° C. and then 1,8-diazabicyclo(5.4.0)undec-7-ene (DBU)(MW=152.2; 38.4 g; 252 mmol) was introduced over about one hour at this temperature. The yellow suspension was stirred for 15 min at around −40° C. and then for 3 h at around 2° C. The medium was poured into the stirred mixture of water (400 ml), ammonium chloride (80 g) and ethyl acetate (140 ml), at around 10° C. The medium was stirred for 30 min, separated by decantation and re-extracted with ethyl acetate. The combined organic phases were washed with water and 1N sodium hydroxide, and dried over sodium sulfate. The medium was concentrated under vacuum and then dichloromethane (300 ml) was introduced. Silica (Merck Si 60; 60 g) was introduced into the solution. The medium was stirred for one hour at around 20° C., the silica was filtered and rinsed with dichloromethane (80 ml). The filtrate was concentrated at atmospheric pressure to 80 ml. The distillation was continued while the volume was kept constant by gradual introduction of isopropanol. The temperature at the end of the exchange was 82° C. The solution was brought to around 20° C., the crystallization was initiated at around 63° C. The suspension was stirred for one hour at around 20° C. The white product was drained at 20° C. and dried under vacuum overnight at around 40° C.: 12.34 g; $C_{20}H_{27}O_2F$; MW=318.4. Yield=61.3%. m.p.=100° C.

IR (CHCl$_3$, cm$^{-1}$): ν 1640, 1610;

$^1$H NMR (CDCl$_3$, ppm): δ 0.66 (d, J=2.5 Hz, 3H), 3.99 (bs, 4H), 4.59 (dd, J=55 and 5 Hz; 1H), 5.60 (m, 1H), from 0.8 to 2.6 (m, 18H);

MS (EI; m/z): 318 (M$^+$), 298 (M$^+$-HF).

Step c: Epoxidation 3,3-Ethylenedioxy-17-alpha-fluoro-5(10)-epoxyestr-9(11)-ene

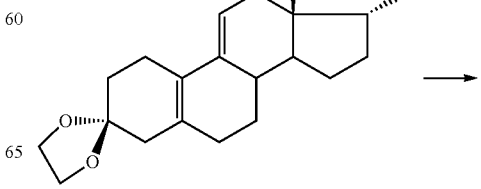

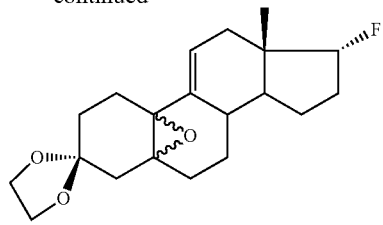

3,3-Ethylenedioxy-17-alpha-fluoroestra-5(10),9(11)-diene (100 g; M: 318.4; 0.314 mol), hexafluoroacetone (trihydrate; 8.75 ml; 0.2 eq.), pyridine (0.1 ml), hydrogen peroxide at 50% (about 18 M; 30 ml; 1.7 eq) and dichloromethane (1000 ml) were vigorously stirred for 18 h at 20-25° C. After reduction in the presence of aqueous sodium thiosulfate, washes (water) and extractions (dichloromethane), the organic phase was concentrated to a total volume of about 400 ml. Next, the dichloromethane was replaced with tetrahydrofuran by continuous distillation at constant volume, until the internal temperature reaches 66° C. The solution obtained was cooled and used as it is in the next step. (HPLC purity: 97%; about 70/30 alpha/beta mixture): $C_{20}H_{27}O_3F$; MW: 334.4. After concentrating to dryness, the alpha-epoxide was crystallized from heptane, and the beta-epoxide was isolated by chromatography on silica of the mother liquors (eluent: cyclohexane 90-ethyl acetate 10). Alpha-epoxide (m.p.=115° C.).

IR (CHCl$_3$, cm$^{-1}$): ν 1642;
$^1$H NMR (CDCl$_3$, ppm): δ 0.66 (d, J=2 Hz, 3H), 3.85 to 3.97 (m, 4H), 4.58 (dd, J=55 and 5 Hz, 1H), 6.07 (dt, J=5.5 and 2.5 Hz, 1H), from 1.15 to 2.57 (m, 18H).

Beta-epoxide (oil):
IR (CHCl$_3$, cm$^{-1}$): ν 1642;
$^1$H NMR (CDCl$_3$, ppm): δ 0.64 (d, J=1.5 Hz, 3H), 3.86 to 3.97 (m, 4H), 4.59 (dd, J=55 and 5 Hz; 1H), 5.88 (dt, J=5.5 and 2 Hz, 1H), from 0.98 to 2.51 (m, 18H).

Step d: Alkylation

Mixture of 17-alpha-fluoro-11-beta-(4-(2-(1-piperidinyl)ethoxy)phenyl)estra-4,9-dien-3-one and 17-alpha-fluoro-1'-(4-(2-(1-piperidinyl)ethoxy)phenyl)-estra-5(10),9(11)-dien-3-one

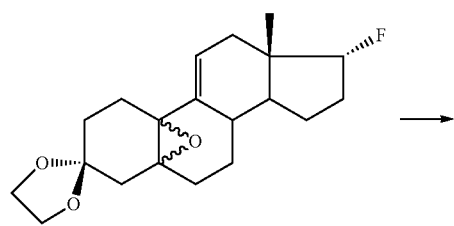

→

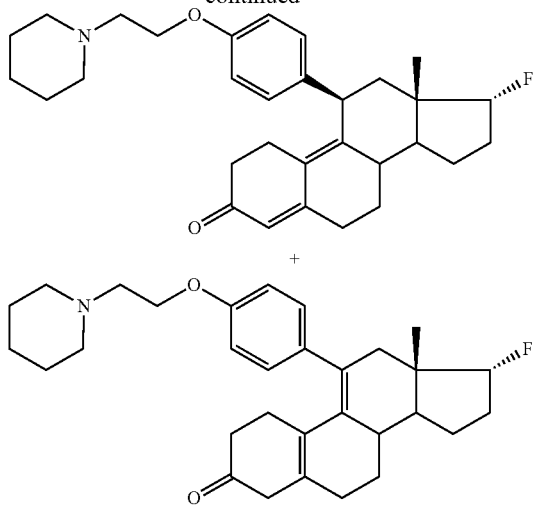

+

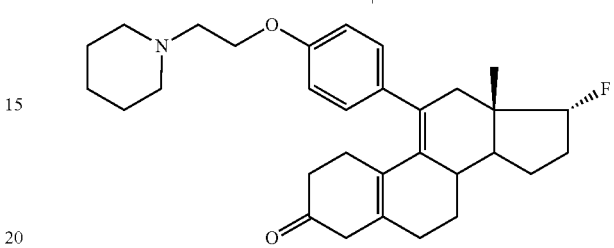

14.4 g of magnesium (turnings; MW=24.3; 593 mmol) were introduced into a reactor, followed by 100 ml of a 1-bromo-4-(2-(1-piperidinyl)ethoxy)benzene solution (153.3 g; MW=284.2; 539 mmol) in THF (560 ml). The medium was heated to around 58° C. and as soon as the medium became gray, the remainder of the solution was introduced at about 58° C. over about 1.5 h, and then further maintained for 2 h at this temperature. The solution was brought to 20° C. and stirred for 18 h. Copper (I) chloride (4.43 g; MW=99.0; 44.7 mmol) was introduced, the medium was stirred for about 15 min at about 20° C. and then the solution of 3,3-ethylenedioxy-17-alpha-fluoro-5(10)-epoxyestr-9(11)-ene (7/3 alpha/beta mixture)(100 g; MW=334.4; 299 mmol) in THF described in the preceding step (step c) was introduced over 30 min at around 20° C. The medium was stirred for one hour at around 20° C. and it was poured over the stirred mixture of ammonium chloride (500 g), water (2 liters) and dichloromethane (1 liter), at around 10° C. The aqueous phase was separated by decantation and re-extracted with dichloromethane. The combined organic phases were washed with water, and then concentrated under vacuum to about 200 ml. The solution was cooled to around 2° C., water (250 ml) and concentrated hydrochloric acid (36%; 150 ml) were introduced, while maintaining the temperature at around 2° C. The medium was stirred for 1.5 h at around 2° C. and then diluted further with water (500 ml), separated by decantation and washed with water to pH>4. The medium was poured over in about 30 min (formation of foam) over a stirred mixture at around 20° C. of sodium bicarbonate (47 g; MW=84.0; 559 mmol) in water (500 ml). The medium was stirred for 30 min and separated by decantation. The aqueous phases were re-extracted with dichloromethane, washed with water and dried over sodium sulfate. The solution was decolorized by adding alumina (around 200 g). The medium was stirred at around 20° C., filtered and rinsed with dichloromethane. The filtrate was concentrated at atmospheric pressure to about 700 ml, and then the distillation was continued while keeping the volume constant by gradual introduction of isopropyl ether. The temperature at the end of the exchange was at 68° C. The crystallization started at around 63° C. The medium was allowed to cool to around 20° C. and the stirring was continued for a further 2 h at around 20° C. The beige product (61.9 g; yield: 43%): 17-alpha-fluoro-11-beta-(4-(2-(1-piperidinyl)ethoxy)phenyl)estra-4,9-dien-3-one is drained: $C_{31}H_{40}FNO_2$; MW: 477.7; m.p.=160° C.;

IR (CHCl$_3$, cm$^{-1}$): 1656, 1608, 1508;

$^1$H NMR (CDCl$_3$, ppm): 0.35 (d, J=2 Hz, 3H); 1.44 (m, 2H); 1.60 (m, 4H); 2.50 (bt, J=6 Hz, 4H); 2.76 (t, 6 Hz, 2H); 4.07 (t, 6 Hz, 2H); 4.39 (m, 1H); 4.46 (dd, J=55.5 and 5 Hz, 1H); 5.76 (bs, 1H); 6.82 and 7.07 (AA'BB', 4H); from 1.2 to 4.1 (m, 18H);

MS (EI; m/z): 477 (M$^+$); 457 (M$^+$-HF); 366; 346; 98.

By chromatography of the mother liquors on silica (eluent: heptane 55-ethyl acetate 40-triethylamine 5), 17-alpha-fluoro-11-(4-(2-(1-piperidinyl)ethoxy)phenyl)-estra-5(10),9(11)-dien-3-one is obtained: C$_{31}$H$_{40}$FNO$_2$; MW: 477.7

IR (CHCl$_3$, cm$^{-1}$): 1710, 1606, 1572, 1507;

$^1$H NMR (CDCl$_3$, ppm): 0.81 (d, J=2 Hz, 3H); 1.46 (m, 2H); 1.62 (m, 4H); 2.53 (m, 4H); 2.80 (m, 2H); 4.10 (t, J=6 Hz, 2H); 4.65 (dd, J=55 and 5, 1H); 6.82 (m, 2H); 7.07 (m, 2H); from 1.1 to 2.85 (m, 18H);

MS (m/z): 478 (MH$^+$); 112.

Step e: Aromatization

3-Acetyl-11-beta-(4-(2-(1-piperidinyl)ethoxy)phenyl)-17-alpha-fluoroestra-1,3,5(10)-triene

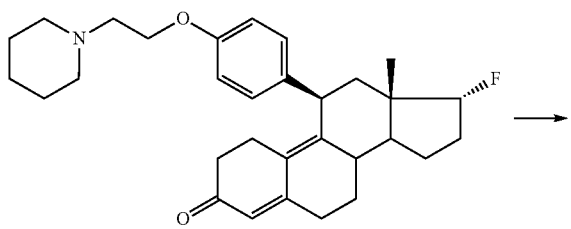

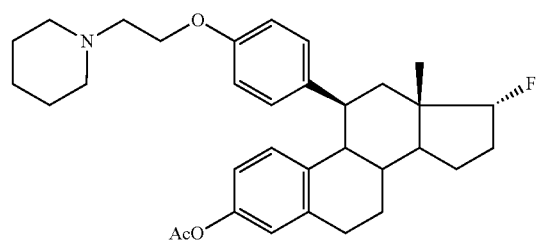

To a solution of 17-alpha-fluoro-11-beta-(4-(2-(1-piperidinyl)ethoxy)phenyl)estra-4,9-dien-3-one (38 g; MW=477.7; 79.5 mmol) (step d) in dichloromethane (152 ml) were added acetic anhydride (MW=102.1; d=1.09; 7.5 ml; 1.0 eq.) and, over 15 min, acetyl bromide (MW=123.0; d=1.66; 14.7 ml; 2.5 eq.) at 20-25° C. (exothermic addition). The brown solution was stirred for 5 h at 20-25° C. The solution was poured over in about 30 min into a sodium hydrogen carbonate suspension (45 g) in water (380 ml) at around 20° C. (emission of carbon dioxide). The mixture was vigorously stirred overnight at around 20° C., and then the organic phase was separated by decantation, washed with 1 N sodium hydroxide (190 ml) and water, and then concentrated to a final volume of 114 ml. The dichloromethane was replaced with methanol at constant volume by distillation under gradual vacuum at about 40° C. The product was stored in solution in methanol. C$_{33}$H$_{42}$FNO$_3$; MW: 519.8.

Step f: Saponification

11-Beta-(4-(2-(1-piperidinyl)ethoxy)phenyl)-17-alpha-fluoroestra-1,3,5(10)-trien-3-ol hydrochloride

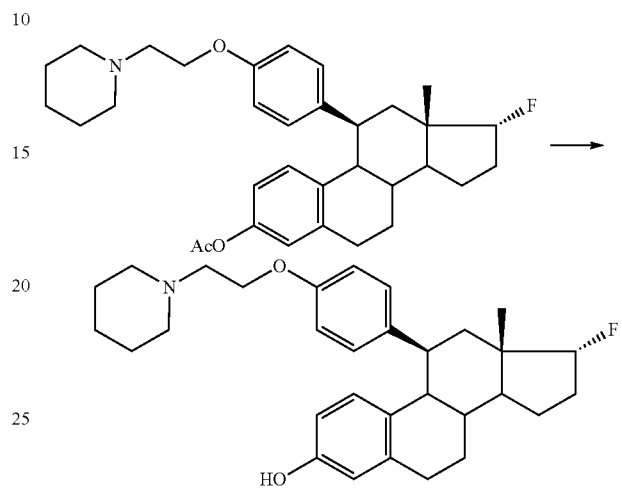

A solution of potassium hydroxide (MW=56.0; 6.7 g; 1.5 eq.) in methanol (76 ml) was added over in about 10 min at around 0° C. to the solution of the fluorinated derivative in methanol obtained in the preceding step e. The medium was stirred for 45 min at 0-5° C., and then poured into water (190 ml) and dichloromethane (190 ml). The organic phase was washed with water. It was acidified by addition of methanol (76 ml), water (190 ml) and hydrochloric acid at 36% (17 ml; 2.2 eq.) and stirred for about 5 min while monitoring the pH (<2). The organic phase was separated by decantation, dried over sodium sulfate, filtered and concentrated until a final volume of 190 ml was obtained. The medium was then distilled at ordinary pressure while keeping the volume constant by gradual introduction of dichloromethane. The expected product crystallized spontaneously. The medium was stirred while allowing it to cool over about 1 h, and then for 2 h, to around 20° C. The product was filtered, washed with dichloromethane and then dried under vacuum at around 40° C. (30.8 g beige solid; yield: 75.3%, HPLC purity: 98%): C$_{31}$H$_{41}$ClFNO$_2$; MW: 514.1;

IR (CHCl$_3$, cm$^{-1}$): ν=3599; 2467; 1609; 1583; 1511.

$^1$H NMR (CDCl$_3$, ppm): 0.22 (d, J=1.5 Hz, 3H); 3.09 (m, 1H); 3.21 (m, 1H); 3.87 (m, 1H); 3.99 (m, 1H); 4.25 (m, 1H); 4.43 (dd, J=56 and 5 Hz, 1H); 6.43 and 6.95 (AA'BB', 4H); 6.60 (dd, J=8.5 and 1.5 Hz, 1H); 6.67 (d, J=1.5 Hz, 1H); 6.78 (d, J=8.5 Hz, 1H); 11.4 (bs, 1H, active); from 0.9 to 3.4 (m, 14H).

MS (ESP; m/z): 478 (MH$^+$).

Step g: Neutralization

11-Beta-(4-(2-(1-piperidinyl)ethoxy)phenyl)-17-alpha-fluoroestra-1,3,5(10)-trien-3-ol Sodium carbonate (MW=106.0; 6.1 g) in aqueous solution (112 ml) was introduced at around 20° C. into a suspension of 11-beta-(4-(2-(1-piperidinyl)ethoxy)phenyl)-17-alpha-fluoroestra-1,3,5(10)-trien-3-ol hydrochloride (28 g;

MW=514.1; 54.5 mmol) (step f) in dichloromethane (224 ml). The medium was stirred for 30 min at around 20° C., separated by decantation and washed with water. The organic phase was dried over sodium sulfate, filtered and the filtrate was concentrated to a residual volume of 140 ml. It was brought to 20° C. and acetone (280 ml) was introduced, followed by silica (Merck Si 60; 42 g). The medium was stirred for one hour at around 20° C., filtered and rinsed with a 2/1 acetone-dichloromethane mixture. The filtrate was concentrated until a final volume of 224 ml was obtained. It was then distilled at atmospheric pressure while the volume was kept constant by gradual introduction of isopropanol. The product crystallized continuously. The medium was stirred while allowing it to cool over about 1 h, and then for 2 h to around 0° C. The product was filtered, washed with isopropanol at around 0° C. and then dried under vacuum at around 40° C. (21.3 g of white solid; m.p.=180° C.; yield: 82.1% HPLC purity: 99%): $C_{31}H_{40}FNO_2$; MW: 477.7;

IR (CHCl$_3$, cm$^{-1}$): ν=3598, 1610, 1581, 1512;

$^1$H NMR (CDCl$_3$, ppm): 0.16 (d, J=2.5 Hz, 3H); 1.34 (m, 2H); 1.44 (m, 4H); 2.37 (m, 4H); 2.56 (t, J=6 Hz, 2H); 3.91 (m, 2H); 3.95 (m, 1H); 4.44 (dd, J=56 and 5 Hz, 1H); 6.31 (dd, J=8.5 and 3 Hz, 1H); 6.46 (d, J=3 Hz, 1H); 6.63 and 6.97 (AA'BB', 4H); 6.71 (d, J=8.5 Hz, 1H); 8.95 (bs, 1H, active); from 0.9 to 3.0 (m, 13H).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A method for preparing compounds of general formula (I):

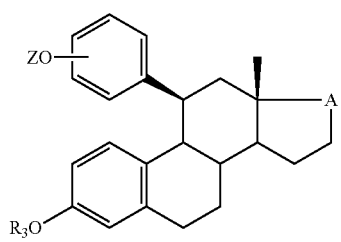

(I)

wherein

Z is a linear alkyl radical or a group R$_4$ of the formula:

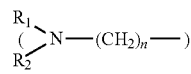

wherein n is an integer from 2 to 8, and

R$_1$ and R$_2$ are identical or different and independently of each other selected from benzyl, linear, branched or cyclic C$_1$-C$_8$alkyl, C$_1$-C$_8$alkenyl or C$_1$-C$_8$alkynyl; or R$_1$ and R$_2$ taken together with the nitrogen atom to which they are attached form a saturated or unsaturated, aromatic or nonaromatic 5- to 6-membered heterocycle optionally containing from 1 to 3 additional heteroatoms and optionally fused with another ring;

A is a keto functional group or a group CH—X, wherein X is a halogen atom;

R$_3$ is hydrogen or a hydroxyl protecting group;

comprising:

a) subjecting a mixture of the compounds of formulae (IIIa) and (IIIb):

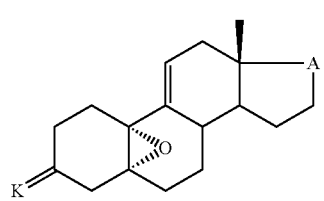

IIIa

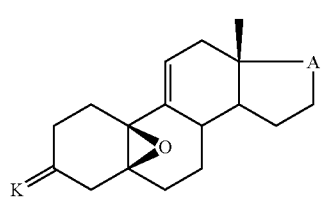

IIIb wherein A is as defined above and =K is a protected keto functional group selected from ketal, thioketal or a mixed ketal, to an alkylation reaction with an organocuprate derivative derived from an organometallic compound of formula R$_5$MgHal or R$_5$Li, Hal being a halogen atom and generated catalytically or stoichiometrically, wherein R$_5$ is:

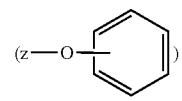

wherein Z is as defined above, the bonding taking place on the phenyl, wherein said mixture of the compounds of formulas (IIIa) and (IIIb) comprises greater than or equal to 30% by weight of the compound of formula (IIIb); and reacting with a suitable deprotecting agent so as to obtain the compounds of formulae (Va), (Vb) and (Vc):

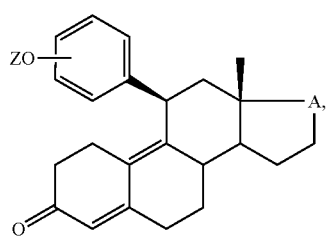

Va

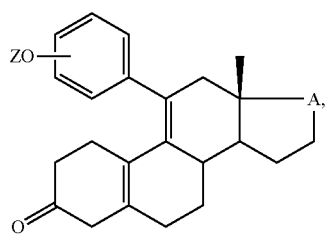

Vb

-continued

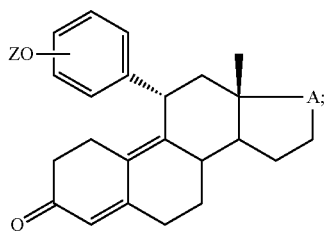

Vc and b) treating the compounds of formulae (Va), (Vb) and (Vc) with a aromatization agent so as to obtain a mixture of the compounds of formulae (VI) and (I):

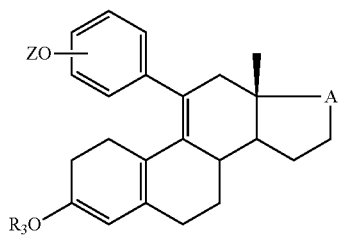

VI which continue to undergo aromatization so as to obtain the compound of formula (I) wherein $R_3$ is as defined above.

2. A method for preparing compounds of general formula (I):

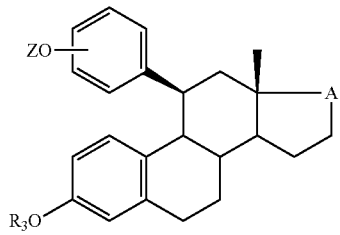

wherein

Z is a linear alkyl radical or a group $R_4$ of the formula:

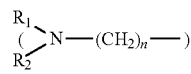

wherein n is an integer from 2 to 8; and $R_1$ and $R_2$ are identical or different and independently of each other selected from benzyl, linear, branched or cyclic $C_1$-$C_8$alkyl, $C_1$-$C_8$alkenyl or $C_1$-$C_8$alkynyl; or $R_1$ and $R_2$ taken together with the nitrogen atom to which they are attached form a saturated or unsaturated, aromatic or nonaromatic 5- to 6-membered heterocycle optionally containing from 1 to 3 additional heteroatoms and optionally fused with another ring;

A is a keto functional group or a group CH—X, wherein X is a halogen atom;

$R_3$ is hydrogen or a hydroxyl protecting group; comprising:

a) subjecting a mixture comprising greater than or equal to 30% of a compound of formula (IIIb):

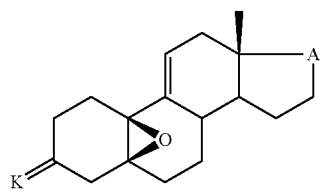

IIIb wherein A is as defined above and =K is a protected keto functional group selected from ketal, thioketal or a mixed ketal, to an alkylation reaction with an organocuprate derivative derived from an organometallic compound of formula $R_5$MgHal or $R_5$Li, Hal being a halogen atom and generated catalytically or stoichiometrically, wherein $R_5$ is:

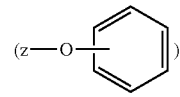

wherein Z is as defined above, the bonding taking place on the phenyl; and reacting with a suitable deprotecting agent so as to obtain the compounds of formulae (Vb) and (Vc):

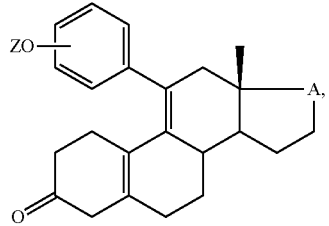

Vb

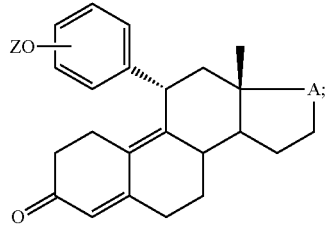

Vc and b) treating the compounds of formulae (Vb) and (Vc) with a aromatization agent so as to obtain the mixture of the compounds of formulae (VI) and (I):

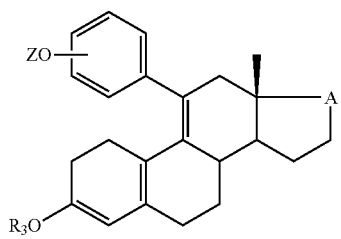

VI which continue to undergo aromatization so as to obtain the compound of formula (I) wherein $R_3$ is as defined above.

3. The method as set forth in claim 1, wherein the compounds of general formula (I) in which A is a keto functional group are prepared comprising the following steps:

a) epoxidizing a compound of formula (II):

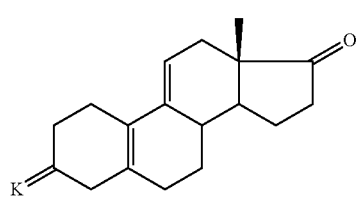

(II)

wherein =K is a protected keto functional group selected from ketal, thioketal or a mixed ketal, so as to obtain the mixture of the alpha and beta isomers of formulae (III'a) and (III'b):

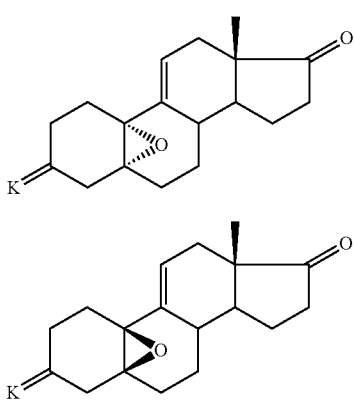

III'a

III'b b) subjecting the mixture of the compounds of formulae (III'a) and (III'b) to an alkylation reaction with an organocuprate derivative derived from an organometallic compound of formula $R_5MgHal$ or $R_5Li$, Hal being a halogen atom and $R_5$ is as defined in claim 1, the bonding taking place on the phenyl; and reacting with a suitable deprotecting agent so as to obtain the compounds of formulae (V' a), (V'b) and (V'c):

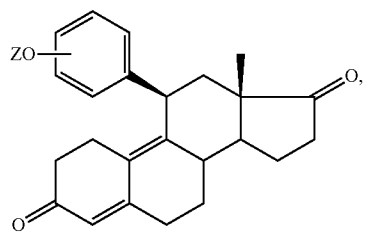

V'a

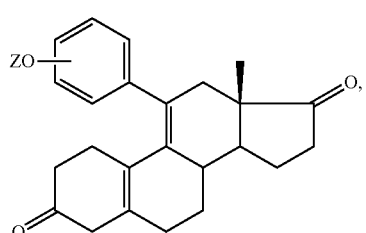

V'b

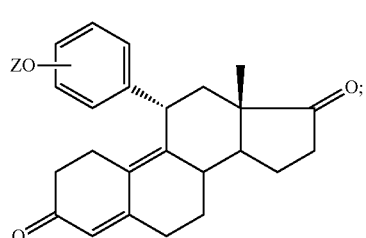

V'c and c) treating the compounds of formulae (V' a), (V'b) and (V'c) with a aromatization agent so as to obtain a mixture of the compounds of formulae (VI') and (I) in which A is a keto functional group:

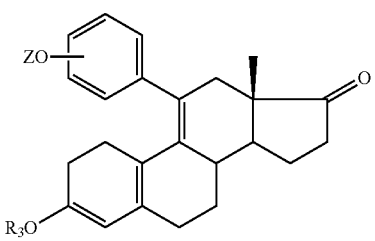

VI' which continue to undergo aromatization so as to obtain the compound of formula (I) in which A is a keto functional group;

d) deprotecting, where appropriate, the product obtained in step c so as to obtain a compound of formula (I) in which A is a keto functional group and $R_3$ is hydrogen; and optionally e) forming a salt of the compound of formula (I) by subjecting it to a salinification reaction.

4. The method as set forth in claim 2, wherein the compounds of general formula (I) in which A is a keto functional group are prepared comprising the following steps:
a) epoxidizing a compound of formula (II):

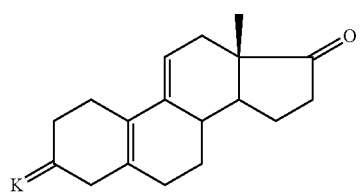

(II)

wherein =K is a protected keto functional group selected from ketal, thioketal or a mixed ketal, so as to obtain the beta isomer of formula (III'b):

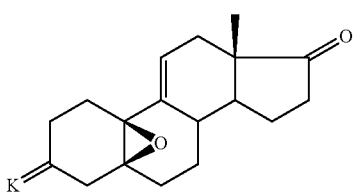

III'b b) subjecting the compound of formula (III'b) to an alkylation reaction with an organocuprate derivative derived from an organometallic compound of formula $R_5MgHal$ or $R_5Li$, Hal being a halogen atom and $R_5$ is as defined in claim 2, the bonding taking place on the phenyl; and reacting with a suitable deprotecting agent so as to obtain the compounds of formulae (V'b) and (V'c):

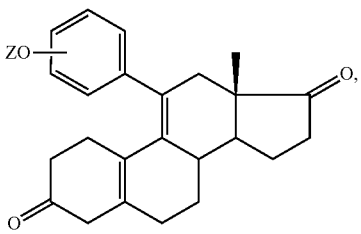

V'b

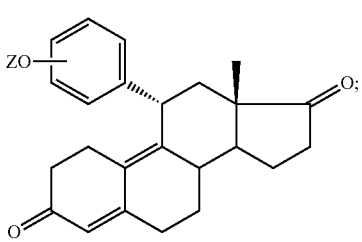

V'c and
c) treating the compounds of formulae (V'b) and (V'c) with a aromatization agent so as to obtain a mixture of the compounds of formulae (VI') and (I) in which A is a keto functional group:

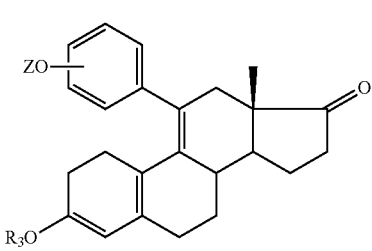

VI' which continue to undergo aromatization so as to obtain the compound of formula (I) in which A is a keto functional group;
d) deprotecting, where appropriate, the product obtained in step c so as to obtain the compound of formula (I) in which A is a keto functional group and $R_3$ is hydrogen; and optionally
e) forming a salt of the compound of formula (I) by subjecting it to a salinification reaction.

5. The method as set forth in claim 3, wherein the alkylation reaction is accompanied by an enolization reaction.

6. The method as set forth in claim 4, wherein the alkylation reaction is accompanied by an enolization reaction.

7. The method as set forth in claim 3, further comprising a step of treating the compounds of formulae (III'a) and (III'b) with a silylating agent in the presence of a base so as to obtain a mixture of silylated enols of formulae (IVa) and (IVb):

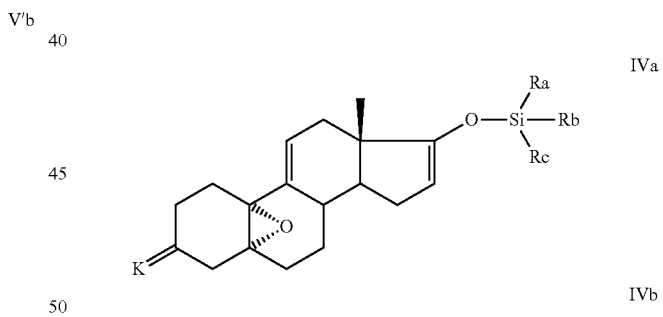

IVa

IVb

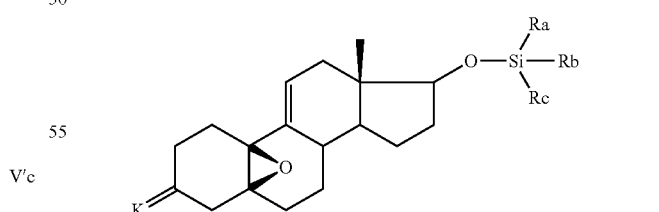

wherein, Ra, Rb and Rc, which are identical or different, represent $C_1$-$C_4$alkyl or phenyl; and
reacting the compounds of formulae (IVa) and (IVb) with an organocuprate derivative as defined in claim 3, the bonding taking place on the phenyl, so as to obtain the compounds of formulae (IV'a) and (IV'b) which are isolated or not isolated:

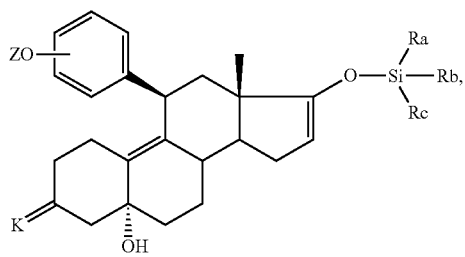

IV'a

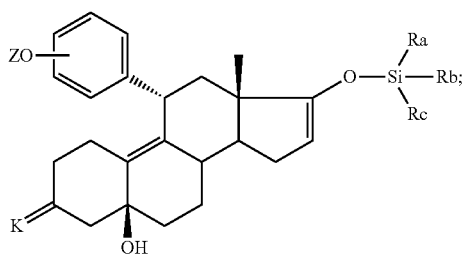

IV'b and deprotecting said products so as to obtain respectively the compounds of formulae (V'a), (V'b) and (V'c) as defined in claim 3.

8. The method as set forth in claim 4, further comprising a step of treating the compound of formula (III'b) with a silylating agent in the presence of a base so as to obtain the silylated enol of formula (IVb):

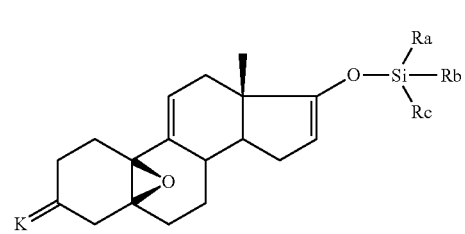

IVb wherein Ra, Rb and Rc, which are identical or different, represent $C_1$-$C_4$alkyl or phenyl; and reacting the compound of formula (IVb) with an organocuprate derivative as defined in claim 4, the bonding taking place on the phenyl, so as to obtain the compound of formula (IV'b) which is isolated or not isolated:

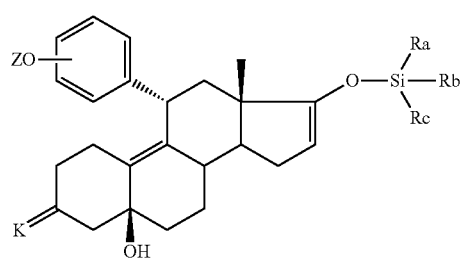

IV'b deprotecting said product so as to obtain respectively the compounds of formulae (V'b) and (V'c) as defined in claim 4.

9. The method as set forth in claim 7, wherein Ra, Rb and Rc are identical and represent a methyl.

10. The method as set forth in claim 8, wherein Ra, Rb and Rc are identical and represent a methyl.

11. The method as set forth in claim 3, wherein =K is a cyclic ketal.

12. The method as set forth in claim 3, wherein =K is 3,3-ethylenedioxy.

13. The method as set forth in claim 4, wherein =K is a cyclic ketal.

14. The method as set forth in claim 4, wherein =K is 3,3-ethylenedioxy.

15. The method as set forth in claim 3, wherein (ZO—) is at the para-position and Z is $R_4$, with n equal to 2.

16. The method as set forth in claim 4, wherein (ZO—) is at the para-position and Z is $R_4$, with n equal to 2.

17. The method as set forth in claim 15, wherein $R_1$ and $R_2$ are identical and represent a linear alkyl group, chosen from methyl or ethyl.

18. The method as set forth in claim 16, wherein $R_1$ and $R_2$ are identical and represent a linear alkyl group, chosen from methyl or ethyl.

19. The method as set forth in claim 3, wherein (ZO—) is at the meta or para position, and Z is methyl.

20. The method as set forth in claim 4, wherein (ZO—) is at the meta or para position, and Z is methyl.

21. The method as set forth in claim 1, wherein compounds of formula (I) in which A is CH—X and Z is $R_4$, are prepared comprising the following steps:

a) subjecting a compound of formula (II):

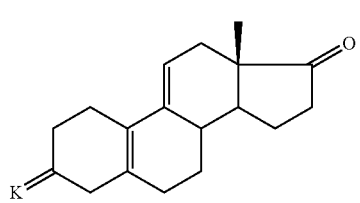

(II)

wherein =K is a protected keto functional group selected from ketal, thioketal or a mixed ketal, to the action of an agent reducing the keto at the 17-position so as to obtain a compound of formula (VII):

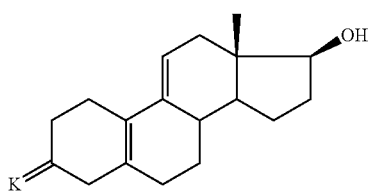

(VII)

b) treating the compound of formula (VII) with a halogenating agent so as to obtain a compound of formula (VIII):

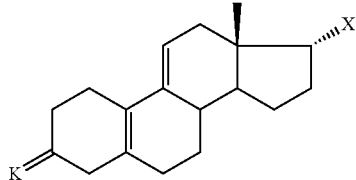

(VIII)

wherein X is halogen;
c) subjecting the compound of formula (VIII) to the action of an epoxidation reagent so as to obtain the mixture of the compounds of formulae (III″a) and (III″b):

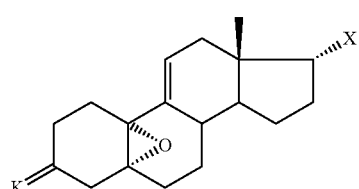

III″a

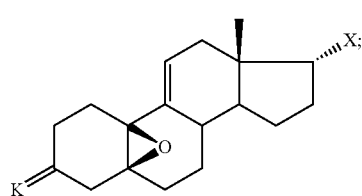

III″b d) subjecting the compounds of formulae (III″a) and (III″b) to an alkylation reaction with an organocuprate derivative derived from an organometallic compound of formula $R_5MgHal$ or $R_5Li$, Hal being a halogen atom and $R_5$ is of the formula:

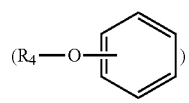

wherein $R_4$ is as defined in claim 1, the bonding taking place on the phenyl; and
subjecting to the action of a deprotecting agent so as to obtain the compounds of formulae (V″a), (V″b) and (V″c):

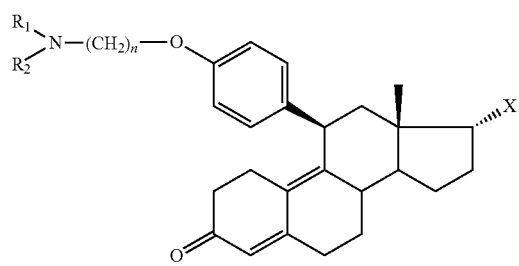

V″a

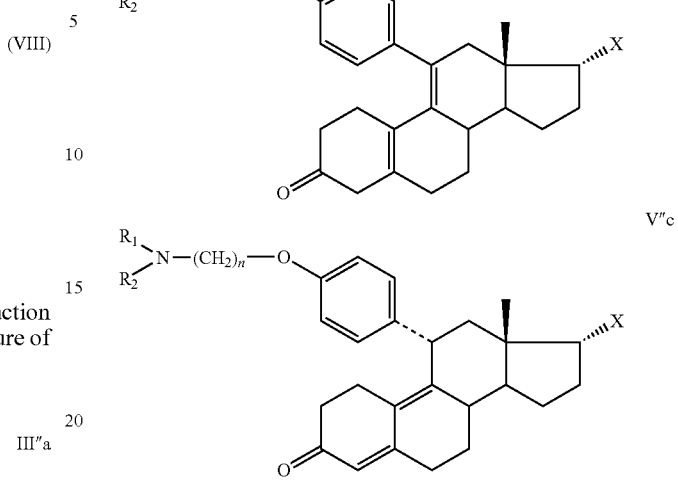

V″b

V″c e) treating the compounds of formulae (V″a), (V″b) and (V″c) with a aromatization agent so as to obtain the mixture of the compounds of formulae (VI″) and (I) in which A represents a group CH—X and Z represents a group $R_4$,

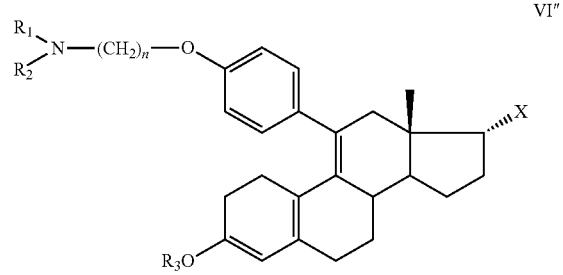

VI″ which continue to undergo aromatization so as to obtain the compound of formula (I) as defined above;
f) deprotecting, where appropriate, the product obtained in step e so as to obtain a compound of formula (I) in which A represents a group CH—X, Z represents a group $R_4$, and $R_3$ is hydrogen; and optionally
forming a salt of the compound of formula (I) by subjecting it to a salinification reaction and neutralization.

22. The method as set forth in claim 1, wherein the aromatization agent is acetyl bromide in the presence of acetic anhydride.

23. The method as set forth in claim 2, wherein the aromatization agent is acetyl bromide in the presence of acetic anhydride.

24. The method as set forth in claim 1, wherein the deprotecting agent used to obtain the compounds of formulae (Va), (Vb), or (Vc) is an agent allowing acid hydrolysis selected from hydrochloric acid or perchloric acid.

25. The method as set forth in claim 2, wherein the deprotecting agent used to obtain the compounds of formulae (Vb) or (Vc) is an agent allowing acid hydrolysis selected from hydrochloric acid or perchloric acid.

26. A method for preparing compounds of general formula (I):

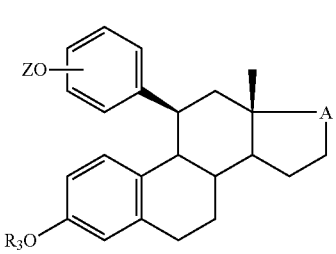

wherein Z is a linear alkyl radical or a group $R_4$ of the formula:

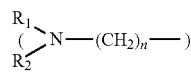

wherein n is an integer from 2 to 8, and $R_1$ and $R_2$ are identical or different and independently of each other selected from benzyl, linear, branched or cyclic $C_1$-$C_8$alkyl, $C_1$-$C_8$alkenyl or $C_1$-$C_8$alkynyl; or $R_1$ and $R_2$ taken together with the nitrogen atom to which they are attached form a saturated or unsaturated, aromatic or nonaromatic 5- to 6-membered heterocycle optionally containing from 1 to 3 additional heteroatoms and optionally fused with another ring;

A is a keto functional group or a group CH—X, wherein X is a halogen atom;

$R_3$ is hydrogen or a hydroxyl protecting group;

comprising:

a) subjecting a mixture of the compounds of formulas (IIIa) and (IIIb):

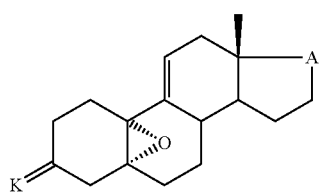

IIIa

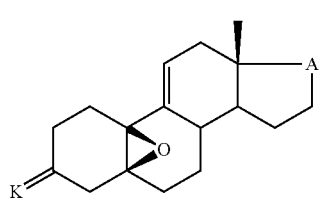

IIIb wherein =K is a protected keto functional group selected from ketal, thioketal or a mixed ketal, to an alkylation reaction with an organocuprate derivative derived from an organometallic compound of formula $R_5$MgHal or $R_5$Li, Hal being a halogen atom and generated catalytically or stoichiometrically, wherein $R_5$ is:

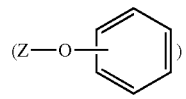

wherein Z is as defined above, the bonding taking place on the phenyl, wherein A is not protected by a silylation reaction prior to said subjecting to said alkylation reaction and said mixture of the compounds of formulas (IIIa) and (IIIb) comprises at least 30% by weight of the compound of formula (IIIb); and reacting with a suitable deprotecting agent so as to obtain the compounds of formulae (Va), (Vb) and (Vc):

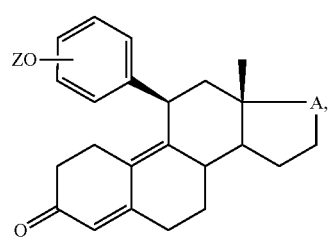

Va

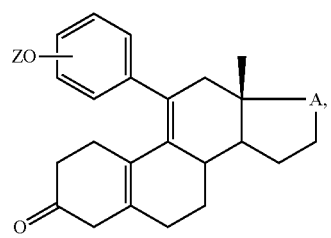

Vb

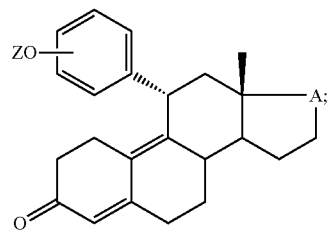

Vc and b) treating the compounds of formulae (Va), (Vb) and (Vc) with a aromatization agent so as to obtain a mixture of the compounds of formulae (VI) and (I):

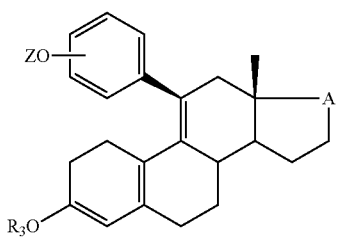

VI which continue to undergo aromatization so as to obtain the compound of formula (I) wherein R₃ is as defined above.

27. The method of claim 26, wherein the compounds of general formula (I) in which A is a keto functional group are prepared comprising the following steps:

a) epoxidizing a compound of formula (II):

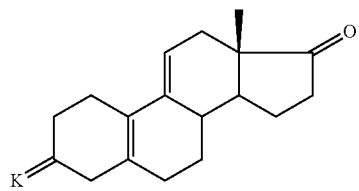
(II)

wherein =K is a protected keto functional group selected from ketal, thioketal or a mixed ketal, so as to obtain the mixture of the alpha and beta isomers of formulae (III'a) and (III'b):

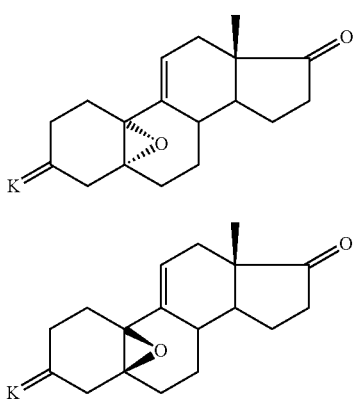
III'a

III'b b) subjecting the mixture of the compounds of formulae (III'a) and (III'b) to an alkylation reaction with an organocuprate derivative derived from an organometallic compound of formula R₅MgHal or R₅Li, Hal being a halogen atom and R₅ is as defined in claim 26, the bonding taking place on the phenyl; and reacting with a suitable deprotecting agent so as to obtain the compounds of formulae (V' a), (V'b) and (V'c):

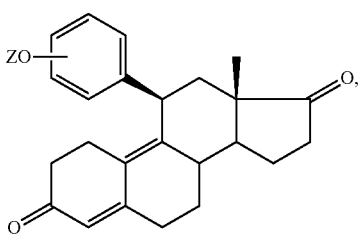
V'a

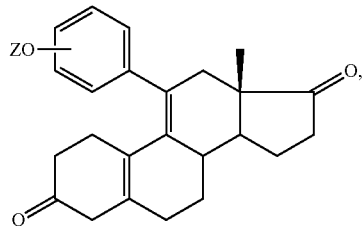
V'b

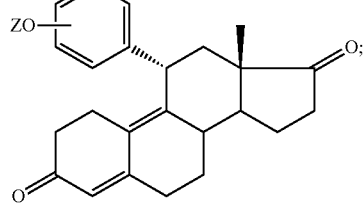
V'c and c) treating the compounds of formulae (V' a), (V'b) and (V'c) with a aromatization agent so as to obtain a mixture of the compounds of formulae (VI') and (I) in which A is a keto functional group:

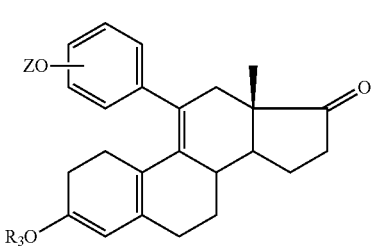
VI' which continue to undergo aromatization so as to obtain the compound of formula (I) in which A is a keto functional group;

d) deprotecting, where appropriate, the product obtained in step c so as to obtain a compound of formula (I) in which A is a keto functional group and R₃ is hydrogen; and optionally e) forming a salt of the compound of formula (I) by subjecting it to a salinification reaction.

28. The method of claim 26, wherein =K is a cyclic ketal.

29. The method of claim 26, wherein =K is 3,3-ethylenedioxy.

30. The method of claim 26, wherein (ZO—) is at the para-position and Z is R₄, with n equal to 2.

31. The method of claim 26, wherein R₁ and R₂ are identical and represent a linear alkyl group, chosen from methyl or ethyl.

* * * * *